(12) United States Patent
Pinto et al.

(10) Patent No.: US 10,881,504 B2
(45) Date of Patent: Jan. 5, 2021

(54) OPHTHALMIC IMPLANTS WITH EXTENDED DEPTH OF FIELD AND ENHANCED DISTANCE VISUAL ACUITY

(71) Applicant: STAAR Surgical Company, Lake Forest, CA (US)

(72) Inventors: Candido Dionisio Pinto, Monrovia, CA (US); Constance Elizabeth Fay, Pasadena, CA (US)

(73) Assignee: STAAR Surgical Company, Lake Forest, CA (US)

( * ) Notice: Subject to any disclaimer, the term of this patent is extended or adjusted under 35 U.S.C. 154(b) by 0 days.

(21) Appl. No.: 15/453,211

(22) Filed: Mar. 8, 2017

(65) Prior Publication Data

US 2017/0258577 A1    Sep. 14, 2017

Related U.S. Application Data

(60) Provisional application No. 62/306,003, filed on Mar. 9, 2016, provisional application No. 62/306,034, filed on Mar. 9, 2016.

(51) Int. Cl.
*A61F 2/16* (2006.01)
*G02C 7/02* (2006.01)

(52) U.S. Cl.
CPC ............ *A61F 2/164* (2015.04); *A61F 2/1602* (2013.01); *A61F 2002/1681* (2013.01); *G02C 7/028* (2013.01); *G02C 2202/22* (2013.01)

(58) Field of Classification Search
CPC .......... A61F 2/164; A61F 2/1613; A61F 2/16; A61F 2/1618; A61F 2002/1681
See application file for complete search history.

(56) References Cited

U.S. PATENT DOCUMENTS 4,199,231 A    4/1980  Evans
4,373,225 A    2/1983  v. Eckardstein et al.
(Continued)

FOREIGN PATENT DOCUMENTS

AU    2015323668    3/2016
BE    1016898       9/2007
(Continued)

OTHER PUBLICATIONS

Atchison, "Design of aspheric intraocular lenses," Ophthal Physiol Opt, Apr. 1991, (vol. 11), (p. 137-146).
(Continued)

*Primary Examiner* — David H Willse
*Assistant Examiner* — Tiffany P Shipmon
(74) *Attorney, Agent, or Firm* — Shay Gtenn LLP; Thomas M. Zlogar

(57) ABSTRACT

A lens configured for implantation into an eye of a human can include an optic including transparent material. The optic can have an anterior surface and a posterior surface. Each of the anterior surface and the posterior surface can have a surface vertex. The optic can have an optical axis through the surface vertices. The lens can also include at least one haptic disposed with respect to the optic to affix the optic in the eye when implanted therein. The anterior and posterior surfaces can include aspheric surfaces. The posterior surface can have an aspheric shape that comprises a biconic offset by perturbations comprising an aspheric higher order function of radial distance from the optical axis. The posterior surface can have an absolute value of ratio $R_x/R_y$ between 0 and 100 and an absolute value of ratio $k_x/k_y$ between 0 and 100.

28 Claims, 8 Drawing Sheets

(56) References Cited

U.S. PATENT DOCUMENTS

| | | |
|---|---|---|
| 4,504,982 A | 3/1985 | Burk |
| 4,525,043 A | 6/1985 | Bronstein |
| 4,529,657 A | 7/1985 | Franz |
| 4,640,595 A | 2/1987 | Volk |
| 4,642,112 A | 2/1987 | Freeman |
| 4,681,102 A | 7/1987 | Bartell |
| 4,710,193 A | 12/1987 | Volk |
| 4,731,079 A | 3/1988 | Stoy |
| 4,752,123 A | 6/1988 | Blaker |
| 4,769,033 A | 9/1988 | Nordan |
| 4,769,035 A | 9/1988 | Kelman |
| 4,787,904 A | 11/1988 | Severin et al. |
| 4,834,750 A | 5/1989 | Gupta |
| 4,981,342 A | 1/1991 | Fiala |
| 4,990,582 A | 2/1991 | Salamone |
| 5,000,676 A | 3/1991 | Fiala |
| 5,019,098 A | 5/1991 | Mercier |
| 5,044,742 A | 9/1991 | Cohen |
| 5,073,021 A | 12/1991 | Marron |
| 5,142,411 A | 8/1992 | Fiala |
| 5,161,964 A | 11/1992 | Frhriere et al. |
| 5,198,844 A | 3/1993 | Roffman et al. |
| 5,217,491 A | 6/1993 | Vanderbilt |
| 5,245,366 A | 9/1993 | Svochak |
| 5,260,727 A | 11/1993 | Oksman et al. |
| 5,286,829 A | 2/1994 | Fedorov et al. |
| 5,290,892 A | 3/1994 | Namdaran et al. |
| 5,329,363 A | 7/1994 | Moskovich |
| 5,331,027 A | 7/1994 | Whitbourne |
| 5,349,396 A | 9/1994 | Roffman et al. |
| 5,359,021 A | 10/1994 | Weinschenk et al. |
| 5,410,375 A | 4/1995 | Fiala |
| 5,436,678 A | 7/1995 | Carroll |
| 5,437,647 A | 8/1995 | Firth et al. |
| 5,480,428 A | 1/1996 | Fedorov et al. |
| 5,485,228 A | 1/1996 | Roffman et al. |
| 5,494,484 A | 2/1996 | Feingold |
| 5,499,987 A | 3/1996 | Feingold |
| 5,517,260 A | 5/1996 | Gladv et al. |
| 5,523,316 A | 6/1996 | Gan et al. |
| 5,574,518 A | 11/1996 | Mercure |
| 5,603,774 A | 2/1997 | LeBoeuf et al. |
| 5,616,148 A | 4/1997 | Eagles et al. |
| 5,620,450 A | 4/1997 | Eagles et al. |
| 5,654,349 A | 8/1997 | Feingold et al. |
| 5,654,363 A | 8/1997 | Feingold et al. |
| 5,654,388 A | 8/1997 | Feingold et al. |
| 5,661,218 A | 8/1997 | Feingold et al. |
| 5,674,282 A | 10/1997 | Cumming |
| 5,684,560 A | 11/1997 | Roffinan et al. |
| 5,693,095 A | 12/1997 | Freeman et al. |
| 5,715,031 A | 2/1998 | Roffman et al. |
| 5,716,364 A | 2/1998 | Makker et al. |
| 5,766,245 A | 6/1998 | Fedorov et al. |
| 5,771,088 A | 6/1998 | Perrott |
| 5,796,462 A | 8/1998 | Roffman et al. |
| 5,800,532 A | 9/1998 | Lieberman |
| 5,814,680 A | 9/1998 | Imafuku et al. |
| 5,822,091 A | 10/1998 | Baker |
| 5,843,186 A | 12/1998 | Christ |
| 5,843,188 A | 12/1998 | McDonald |
| 5,847,802 A | 12/1998 | Menezes et al. |
| 5,856,120 A | 1/1999 | Fedorov et al. |
| 5,864,378 A | 1/1999 | Portnev |
| 5,882,421 A | 3/1999 | LeBoeuf et al. |
| 5,910,537 A | 6/1999 | Feingold et al. |
| 5,913,989 A | 6/1999 | Wycliffe et al. |
| 5,922,821 A | 7/1999 | LeBoeuf et al. |
| 5,929,969 A | 7/1999 | Roffman |
| 5,947,975 A | 9/1999 | Kikuchi et al. |
| 5,982,543 A | 11/1999 | Fiala |
| 6,024,447 A | 2/2000 | Portnev |
| 6,036,891 A | 3/2000 | Liao et al. |
| 6,045,578 A | 4/2000 | Collins et al. |
| 6,106,553 A | 8/2000 | Feingold |
| 6,110,202 A | 8/2000 | Barraquer et al. |
| 6,120,148 A | 9/2000 | Fiala et al. |
| 6,126,286 A | 10/2000 | Portney |
| 6,150,472 A | 11/2000 | Engbers |
| 6,148,862 A | 12/2000 | Patel et al. |
| 6,165,490 A | 12/2000 | Fedorov et al. |
| 6,179,420 B1 | 1/2001 | Roffman et al. |
| 6,203,973 B1 | 3/2001 | Chen et al. |
| 6,238,975 B1 | 5/2001 | Fliesler et al. |
| 6,241,766 B1 | 6/2001 | Liao et al. |
| 6,244,709 B1 | 6/2001 | Vavntraub et al. |
| 6,245,106 B1 | 6/2001 | Makker et al. |
| 6,271,281 B1 | 8/2001 | Liao et al. |
| 6,386,357 B1 | 5/2002 | Egawa |
| 6,398,809 B1 | 6/2002 | Hoffmann et al. |
| 6,457,826 B1 | 10/2002 | Lett |
| 6,488,708 B2 | 12/2002 | Sarfarazi |
| 6,500,181 B1 | 12/2002 | Portney |
| 6,506,212 B2 | 1/2003 | Zhou et al. |
| 6,520,638 B1 | 2/2003 | Roffman et al. |
| 6,533,416 B1 | 3/2003 | Fermigier et al. |
| 6,536,899 B1 | 3/2003 | Fiala |
| 6,537,317 B1 | 3/2003 | Steinert et al. |
| 6,547,822 B1 | 4/2003 | Lang |
| 6,557,998 B2 | 5/2003 | Portney |
| 6,576,011 B2 | 6/2003 | Portney |
| 6,576,012 B2 | 6/2003 | Lang |
| 6,609,793 B2 | 8/2003 | Norrby et al. |
| 6,709,103 B1 | 3/2004 | Roffman et al. |
| 6,737,448 B2 | 5/2004 | Liao |
| 6,790,232 B1 | 9/2004 | Lang |
| 6,802,606 B2 | 10/2004 | Roffman et al. |
| 6,824,563 B2 | 11/2004 | Lang |
| 6,899,425 B2 | 5/2005 | Roffman et al. |
| 6,923,539 B2 | 8/2005 | Simoson et al. |
| 6,957,891 B2 | 10/2005 | Fiala |
| 7,036,931 B2 | 5/2006 | Lindacher et al. |
| 7,057,816 B1 | 6/2006 | Allen et al. |
| 7,061,693 B2 | 6/2006 | Zalevsky |
| 7,073,906 B1 | 7/2006 | Portney |
| 7,118,214 B2 | 10/2006 | Cox |
| 7,157,538 B2 | 1/2007 | Callaghan et al. |
| 7,178,918 B2 | 2/2007 | Griffin |
| 7,261,412 B2 | 8/2007 | Somani et al. |
| 7,543,937 B2 | 6/2009 | Piers et al. |
| 7,789,910 B2 | 9/2010 | Knox et al. |
| 7,828,431 B2 | 11/2010 | Ho et al. |
| 7,871,162 B2 | 1/2011 | Weeber |
| 7,918,886 B2 | 4/2011 | Aharoni et al. |
| 7,997,727 B2 | 8/2011 | Ho et al. |
| 8,066,767 B2 | 11/2011 | Fiala et al. |
| 8,231,219 B2 | 7/2012 | Weeber |
| 8,425,597 B2 | 4/2013 | Glick et al. |
| 8,485,662 B2 | 7/2013 | Collins et al. |
| 8,486,055 B2 | 7/2013 | Knox et al. |
| 8,580,228 B2 | 7/2013 | Weeber |
| 8,562,675 B2 | 10/2013 | Hong et al. |
| 8,617,147 B2 | 12/2013 | Knox et al. |
| 8,740,978 B2 | 6/2014 | Weeber et al. |
| 8,747,466 B2 | 6/2014 | Weeber et al. |
| 8,862,447 B2 | 10/2014 | Weeber |
| 8,894,204 B2 | 11/2014 | Weeber et al. |
| 8,911,086 B2 | 12/2014 | Dai |
| 8,974,526 B2 | 3/2015 | Bogaert |
| 9,060,847 B2 | 6/2015 | Smith et al. |
| 9,101,466 B2 | 8/2015 | Hong |
| 9,144,491 B2 | 9/2015 | Knox et al. |
| 9,195,074 B2 | 11/2015 | Bakaraju et al. |
| 9,201,250 B2 | 12/2015 | Bakaraju et al. |
| 9,216,080 B2 | 12/2015 | Bogaert et al. |
| 9,220,591 B2 | 12/2015 | Zhao |
| RE45,969 E | 4/2016 | Hong et al. |
| 9,301,833 B2 | 4/2016 | Gulati et al. |
| 9,329,408 B2 | 5/2016 | Matsunaga et al. |
| 9,454,018 B2 | 9/2016 | Weeber et al. |
| 9,535,263 B2 | 1/2017 | Bakaraju et al. |
| 9,541,773 B2 | 1/2017 | Bakaraju et al. |
| 9,545,340 B1 | 1/2017 | Knox et al. |
| 9,557,579 B2 | 1/2017 | Lindacher et al. |

(56) References Cited

U.S. PATENT DOCUMENTS

| | | |
|---|---|---|
| 9,636,216 B2 | 5/2017 | Ossipov et al. |
| 9,690,882 B2 | 7/2017 | Dobschal |
| 9,717,628 B2 | 8/2017 | Vidal Canovas et al. |
| 9,823,493 B2 | 11/2017 | Caldarise et al. |
| 10,117,775 B2 | 11/2018 | Gulati et al. |
| 2001/0044657 A1 | 11/2001 | Kellan |
| 2002/0120330 A1 | 8/2002 | Galin |
| 2003/0014107 A1 | 1/2003 | Reynard |
| 2003/0063254 A1 | 4/2003 | Piers |
| 2003/0081171 A1 | 5/2003 | Griffin |
| 2003/0097177 A1 | 5/2003 | Tran et al. |
| 2003/0103187 A1 | 6/2003 | Miyamura et al. |
| 2003/0187505 A1 | 10/2003 | Liao |
| 2004/0087963 A1 | 5/2004 | Ossipov et al. |
| 2005/0027354 A1 | 2/2005 | Brady et al. |
| 2005/0125000 A1 | 6/2005 | Tourrette et al. |
| 2005/0147735 A1 | 7/2005 | Lowery et al. |
| 2005/0259222 A1 | 11/2005 | Kelch et al. |
| 2006/0089712 A1 | 4/2006 | Malecaze |
| 2006/0095127 A1 | 5/2006 | Feingold et al. |
| 2006/0098162 A1 | 5/2006 | Bandhauer et al. |
| 2006/0098163 A1 | 5/2006 | Bandhauer et al. |
| 2006/0116763 A1 | 6/2006 | Simpson |
| 2006/0167545 A1 | 7/2006 | Fiala et al. |
| 2006/0176572 A1 | 8/2006 | Fiala |
| 2006/0187413 A1 | 8/2006 | Applegate et al. |
| 2006/0200167 A1 | 9/2006 | Peterson et al. |
| 2006/0244904 A1 | 11/2006 | Hong et al. |
| 2006/0244906 A1 | 11/2006 | Piers et al. |
| 2007/0000801 A1 | 1/2007 | Mauran et al. |
| 2007/0002274 A1 | 1/2007 | Somani et al. |
| 2007/0168028 A1 | 7/2007 | Tran et al. |
| 2007/0258143 A1 | 11/2007 | Portney |
| 2008/0013043 A1 | 1/2008 | Ye et al. |
| 2008/0086208 A1 | 4/2008 | Nordan |
| 2008/0114373 A1 | 5/2008 | Rathert |
| 2008/0225409 A1 | 9/2008 | Alexay |
| 2009/0059163 A1 | 3/2009 | Pinto |
| 2009/0112313 A1 | 4/2009 | Mentak |
| 2009/0157179 A1 | 6/2009 | Pinto et al. |
| 2009/0210054 A1 | 8/2009 | Weeber et al. |
| 2009/0279048 A1* | 11/2009 | Hong ............... A61F 2/1613 351/159.21 |
| 2010/0057202 A1* | 3/2010 | Bogaert ............ A61F 2/1618 623/6.27 |
| 2010/0079723 A1 | 4/2010 | Kingston et al. |
| 2010/0087921 A1* | 4/2010 | Simpson ............ A61F 2/164 623/6.24 |
| 2010/0100177 A1 | 4/2010 | Zhao |
| 2010/0125279 A1 | 5/2010 | Karakelle et al. |
| 2010/0131059 A1 | 5/2010 | Callahan et al. |
| 2010/0161051 A1 | 6/2010 | Hong |
| 2010/0188636 A1 | 7/2010 | Pinto et al. |
| 2011/0046634 A1 | 2/2011 | Rathert |
| 2011/0218623 A1* | 9/2011 | Dishler ............. A61F 2/145 623/5.11 |
| 2011/0313519 A1 | 12/2011 | Cumming |
| 2011/0313525 A1 | 12/2011 | Cumming |
| 2012/0071888 A1 | 3/2012 | Putallaz et al. |
| 2012/0136438 A1 | 5/2012 | Moriarty |
| 2013/0090730 A1 | 4/2013 | Weeber et al. |
| 2013/0226294 A1 | 8/2013 | Van Der Mooren et al. |
| 2013/0278888 A1 | 10/2013 | Bakaraju et al. |
| 2014/0022508 A1 | 1/2014 | Ben-Yaish et al. |
| 2014/0104563 A1 | 4/2014 | Bakaraju et al. |
| 2014/0135919 A1 | 5/2014 | Gontijo et al. |
| 2014/0135921 A1 | 5/2014 | Robert et al. |
| 2014/0155999 A1 | 6/2014 | Vidal Canovas et al. |
| 2014/0200588 A1 | 7/2014 | Anderson et al. |
| 2015/0182329 A1 | 7/2015 | Bogaert |
| 2015/0366656 A1 | 12/2015 | Wortz et al. |
| 2016/0067035 A1 | 3/2016 | Gontijo et al. |
| 2016/0116764 A1 | 4/2016 | Newman |
| 2016/0193037 A1* | 7/2016 | Pinto ............... A61F 2/1613 623/6.23 |
| 2016/0193040 A1 | 7/2016 | Qureshi et al. |
| 2016/0198942 A1 | 7/2016 | Dai |
| 2016/0302916 A1 | 10/2016 | Sarver et al. |
| 2016/0320633 A1 | 11/2016 | Weeber |
| 2016/0324629 A1 | 11/2016 | Sandstedt et al. |
| 2016/0346076 A1 | 12/2016 | Paul et al. |
| 2017/0007396 A1 | 1/2017 | Weeber et al. |
| 2017/0102556 A1 | 4/2017 | Lindacher et al. |
| 2017/0196682 A1 | 7/2017 | Lawu |
| 2017/0245983 A1 | 8/2017 | Hong et al. |
| 2017/0245987 A1 | 8/2017 | Canovas Vidal et al. |
| 2017/0276963 A1 | 9/2017 | Brennan et al. |
| 2017/0290657 A1 | 10/2017 | Luque |
| 2017/0319332 A1 | 11/2017 | Kahook et al. |
| 2017/0325937 A1 | 11/2017 | Weeber et al. |
| 2017/0326002 A1 | 11/2017 | Canovas Vidal et al. |
| 2020/0085567 A1 | 3/2020 | Pinto et al. |

FOREIGN PATENT DOCUMENTS

| | | |
|---|---|---|
| CN | 1575146 A | 2/2005 |
| CN | 1671336 A | 9/2005 |
| CN | 1835719 A | 9/2006 |
| CN | 1845712 A | 10/2006 |
| CN | 101039635 A | 9/2007 |
| CN | 101073519 A | 11/2007 |
| CN | 101199437 A | 6/2008 |
| CN | 101252895 A | 8/2008 |
| CN | 101437468 A | 5/2009 |
| CN | 101490600 A | 7/2009 |
| CN | 101796451 A | 8/2010 |
| CN | 102106764 A | 6/2011 |
| CN | 202086618 U | 12/2011 |
| EP | 0 470 811 | 2/1992 |
| EP | 485197 A1 | 5/1992 |
| EP | 0 503 111 | 9/1992 |
| EP | 0 742 466 | 7/2003 |
| EP | 1 402 852 | 3/2004 |
| EP | 1 424 049 | 6/2004 |
| EP | 1 862 148 | 12/2007 |
| EP | 1958593 A1 | 8/2008 |
| FR | 2745711 A1 | 9/1997 |
| JP | 63-310820 A | 12/1988 |
| JP | 64-002644 A | 1/1989 |
| JP | H07-184989 A | 7/1995 |
| JP | 2001235712 A | 8/2001 |
| JP | 2005002377 A | 1/2005 |
| JP | 2005523981 A | 8/2005 |
| JP | 2006522674 A | 10/2006 |
| JP | 2005062965 A | 6/2007 |
| JP | 2007536047 A | 12/2007 |
| JP | 2009525835 A | 7/2009 |
| JP | 2009528855 A | 8/2009 |
| JP | 2012517029 A | 7/2012 |
| KR | 101030689 B1 | 4/2011 |
| KR | 10-1248488 B1 | 4/2013 |
| WO | WO94/07436 A1 | 4/1994 |
| WO | WO 94/13225 | 6/1994 |
| WO | WO94/025510 A1 | 11/1994 |
| WO | WO96/040303 A1 | 12/1996 |
| WO | WO 97/26843 | 7/1997 |
| WO | WO97/35896 A1 | 10/1997 |
| WO | WO 98/03894 | 1/1998 |
| WO | WO 99/57720 | 11/1999 |
| WO | WO 01/10354 | 2/2001 |
| WO | WO01/071392 A1 | 9/2001 |
| WO | WO 01/89424 | 11/2001 |
| WO | WO 02/051338 | 7/2002 |
| WO | WO 03/101355 | 12/2003 |
| WO | WO 04/095187 | 11/2004 |
| WO | WO 05/046527 | 5/2005 |
| WO | WO 05/099630 | 10/2005 |
| WO | WO 06/014624 | 2/2006 |
| WO | WO 06/018834 | 2/2006 |
| WO | WO 06/056847 | 6/2006 |
| WO | WO 06/100086 | 9/2006 |
| WO | WO 06/108005 | 10/2006 |

(56) References Cited

FOREIGN PATENT DOCUMENTS

| WO | WO 07/137100 | 11/2007 |
|---|---|---|
| WO | WO 08/065573 | 6/2008 |
| WO | WO 08/077006 | 6/2008 |
| WO | WO 08/080464 | 7/2008 |
| WO | WO2009/029481 A1 | 3/2009 |
| WO | WO 09/130610 | 10/2009 |
| WO | WO 10/100523 | 9/2010 |
| WO | WO 11/135685 | 11/2010 |
| WO | WO2010/135685 A1 | 11/2010 |
| WO | WO 11/153158 | 12/2011 |
| WO | WO2012/015300 A1 | 2/2012 |
| WO | WO 12/083143 | 6/2012 |
| WO | WO 13/028992 | 2/2013 |
| WO | WO2013/159045 A1 | 10/2013 |
| WO | WO 16/025315 | 2/2016 |
| WO | WO 16/040331 | 3/2016 |
| WO | WO2016/040331 A1 | 3/2016 |
| WO | WO 16/145068 | 9/2016 |
| WO | WO 16/167906 | 10/2016 |
| WO | WO 17/149401 | 9/2017 |
| WO | WO 17/156077 | 9/2017 |

OTHER PUBLICATIONS

Liou L. H. et al., "Anatomically accurate, finite model eye for optical modeling," Journal of the Optical Society of America, Optical Society of America (US), vol. 14, No. 8, pp. 1684-1695, Aug. 1997.

"Visual performance when it's needed most—AcrySof® IQ IOL BioMaterial Advantage," (Alcon) Printed Jun. 7, 2017 from URL:https://www.myalcon.com/products/surgical/acrysof-ig-iol-biomaterial.shtml.

Southall, James P.C., "Objective of Microscope," Mirrors Prisms & Lenses, 1933, (p. 675-677).

Smith, Warren J., "Improving a Design," Modem Lens Design, 1992, (p. 291-295).

An Introduction to Chromatic Aberration in Refractors, "www.maa.mhn.de/ scholar/ chromatic_ aberration.html," printed Feb. 26, 2009.

Flat Schmidt Camera, "www.5f.biglobe.ne.jp/-kztanaka/flatschmidtcamera.html," printed Feb. 26, 2009.

Spherochromatism Definition, "Answers.com," printed Feb. 26, 2009.

Telescope optics.net, "Secondary Spectrum and Spherochromatism, www.telescope-optics.net/secondary spectrum_spherochromatism.htm," printed Feb. 26, 2009.

Pfaff, Bob, "Guide to Making Schmidt Correctors," www.considine.net/drowsemi/pfaff/pfaff.htm, printed Feb. 26, 2009.

Telescope Optics.Net, "Full-aperture Schmidt Corrector: Schmidt Camera," www.telescope-optics.net/Schmidt-camera.htm, printed Feb. 26, 2009.

Schmidt Camera Definition, en.wikipedia.org/wiki/Schmidt_camera, printed Feb. 26, 2009.

Christensen, Mark, "Bernard Schmidt: His Camera and Its Derivatives," www.fvastro.org/articles/schmidtp2.htm, printed Feb. 26, 2009. Archive date Jul. 30, 2012, copyright date 2001.

Smith, Warren J., "Sec. 3.7, Aberration Correction and Residuals," Modem Optical Eng., 1990, p. 76-79.

Smith, Warren J., "Sec. 12.5, Achromatic Objectives (Design Forms)," Modem Optical Eng., 1990, p. 375-384.

Thibos, Larry N., "Retinal Image Quality and Visual Performance," Wavefront Congress Short Course, Feb. 2008 in 40 pages.

European Extended Search Report, re Application No. 15839905.5, dated Apr. 16, 2018.

International Search Report and Written Opinion, re PCT Application No. PCT/US2008/073848 dated Nov. 21, 2008.

International Search Report and Written Opinion, re PCT Application No. PCT/US2008/086362 dated Mar. 31, 2009.

International Search Report and Written Opinion, re PCT Application No. PCT/US15/48961, dated Jan. 28, 2016.

International Search Report and Written Opinion, re PCT Application No. PCT/US17/21291, dated Jun. 16, 2017.

Greenwall; Glass versus polycarbonate; 3 pages; retrieved from the internet (http://www.greenwallsolutions.com/installation/glass-vs-polycarbonate/) on Oct. 2012.

Ophthalmo Pharma; Solo Pre-Loaded IOL Injector; 11 pages; Jul. 2010.

Paul et al.; U.S. Appl. No. 16/004,060 entitled "Controlled axial displacement posterior chamber phakic intraocular lens," filed Jun. 8, 2018.

Pinto; U.S. Appl. No. 16/126,806 entitled "Methods of providing extended depth of field and/or enhanced distance visual acuity," filed Sep. 10, 2018.

Ossipov et al.; U.S. Appl. No. 15/583,758 entitled "Injector cartridge with improved lubricity," filed May 1, 2017.

Altissimo; E-beam lithography for micro-nanofabrication; Biomicrofluidics; 4(2); 026503; doi: 10.1063/1.3437589; 6 pages; Jun. 15, 2010.

Malyugin et al.; Gradient refractive index optics IOL: theroretical background and clinical results; Middle East African Journal of Ophthalmology; 21(1); pp. 32-39; 22 pages (Author Manuscript); Jan. 2014.

Ossipov et al.; U.S. Appl. No. 16/544,567 entitled "Polymeric composition exhibiting nanogradient of refractive index," filed Aug. 19, 2019.

Pinto et al.; U.S. Appl. No. 16/818,970 entitled "Ophthalmic implants with extended depth of field and/or enhanced distance visual acuity," filed Mar. 13, 2020.

* cited by examiner

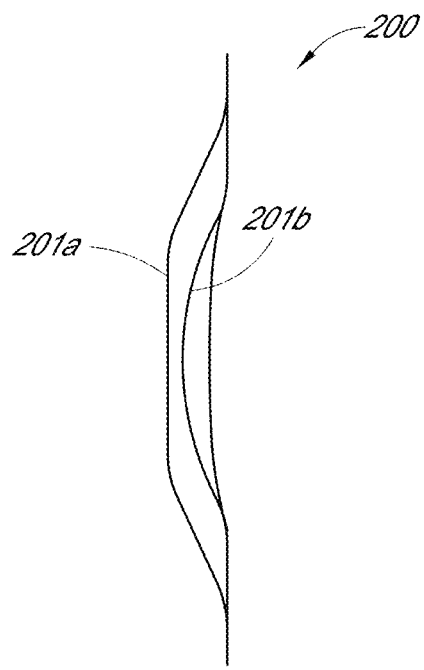
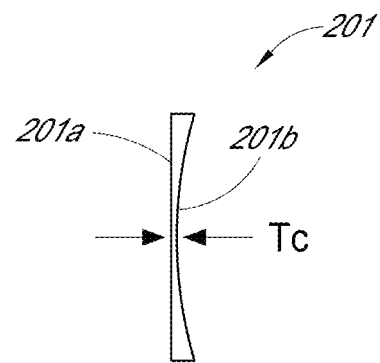
FIG. 3B    FIG. 4
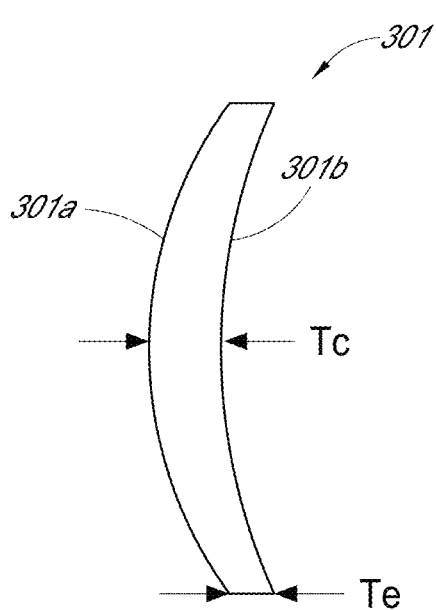
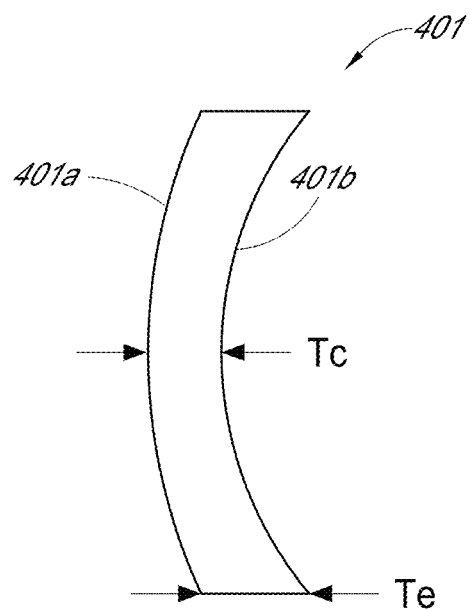
FIG. 5A    FIG. 5B

OPHTHALMIC IMPLANTS WITH EXTENDED DEPTH OF FIELD AND ENHANCED DISTANCE VISUAL ACUITY

INCORPORATION BY REFERENCE TO ANY PRIORITY APPLICATIONS

This application claims the benefit of priority of U.S. Provisional Application No. 62/306,003, filed on Mar. 9, 2016, and U.S. Provisional Application No. 62/306,034, filed on Mar. 9, 2016. The entire disclosures of each of the prior applications are hereby expressly incorporated by reference.

BACKGROUND

Field of the Invention

This disclosure relates to ophthalmic implants, for example, to ophthalmic implants with extended depth of field.

Description of the Related Art

FIG. 1 is a schematic illustration of the human eye. As shown in FIG. 1, the human eye 100 includes a cornea 110, an iris 115, a natural crystalline lens 120, and a retina 130. Light enters the eye 100 through the cornea 110 and towards the pupil, which is the opening in the center of the iris 115. The iris 115 and pupil help regulate the amount of light entering the eye 100. In bright lighting conditions, the iris 115 closes the pupil to let in less light, while in dark lighting conditions, the iris 115 opens the pupil to let in more light. Posterior to the iris 115 is a natural crystalline lens 120. The cornea 110 and the crystalline lens 120 refract and focus the light toward the retina 130. In an eye 100 with a visual acuity of 20/20, the crystalline lens 120 focuses the light to the back of the eye onto the retina 130. The retina 130 senses the light and produces electrical impulses, which are sent through the optic nerve 140 to the brain. When the eye does not properly focus the light, corrective and/or artificial lenses have been used.

SUMMARY

Certain embodiments described herein include a lens configured for implantation into an eye of a human. The lens can include an optic comprising transparent material. The lens can also include haptic portions disposed about the optic to affix the optic in the eye when implanted therein. The optic can include an anterior surface and a posterior surface. The anterior surface can be convex and the posterior surface can be concave such that the optic is meniscus shaped. Each of the convex anterior surface and the concave posterior surface can have a surface vertex. The optic can have an optical axis through the surface vertices. In various embodiments, a thickness along the optical axis can be between about 100-700 micrometers (or any range formed by any of the values in this range). In addition, the anterior and posterior surfaces can comprise aspheric surfaces.

Certain embodiments described herein include a lens configured for implantation into an eye of a human. The lens can include an optic comprising transparent material. The lens can also include at least one haptic disposed with respect to the optic to affix the optic in the eye when implanted therein. The optic can have an anterior surface and a posterior surface. The anterior surface can be convex and the posterior surface can be concave such that the optic is meniscus shaped. Each of the convex anterior surface and the concave posterior surface can have a surface vertex. The optic can have an optical axis through the surface vertices. In various embodiments, the anterior and posterior surfaces can comprise aspheric surfaces. The anterior surface can have an aspheric shape that comprises a conic or biconic offset by perturbations comprising an aspheric higher order function of radial distance from the optical axis.

In some such embodiments, the aspheric higher order function can include at least one even order term, $a_{2n}r^{2n}$, where n is an integer and $a_{2n}$ is a coefficient and r is the radial distance from the optical axis. For example, the aspheric higher order function can include a second order term, $a_2r^2$, where $a_2$ is a coefficient and r is the radial distance from the optical axis. As another example, the aspheric higher order function can include a fourth order term, $a_4r^4$, where $a_4$ is a coefficient and r is the radial distance from the optical axis. The aspheric higher order function also can include a sixth order term, $a_6r^6$ where $a_6$ is a coefficient and r is the radial distance from the optical axis. Furthermore, the aspheric higher order function can include an eighth order term, $a_8r^8$ where $a_8$ is a coefficient and r is the radial distance from the optical axis. In some embodiments of the lens, the optic can have a thickness along the optical axis that is between about 100-700 microns (or any range formed by any of the values in this range). In various embodiments, the anterior surface has an aspheric shape that comprises a biconic offset by the perturbations.

Certain embodiments described herein include a lens configured for implantation into an eye of a human. The lens can include an optic comprising transparent material. The lens can also include at least one haptic disposed with respect to the optic in the eye when implanted therein. The optic can have an anterior surface and a posterior surface. The anterior surface can be convex and the posterior surface can be concave such that the optic is meniscus shaped. Each of the convex anterior surface and the concave posterior surface can have a surface vertex. The optic can have an optical axis through the surface vertices. In various embodiments, the anterior and posterior surfaces can comprise aspheric surfaces. The posterior surface can have an aspheric shape that comprises a conic or biconic offset by perturbations comprising an aspheric higher order function of radial distance from the optical axis. In various embodiments, the posterior surface has an aspheric shape that comprises a biconic offset by the perturbations.

Certain embodiments described herein include a lens configured for implantation into an eye of a human. The lens can include an optic comprising transparent material. The optic can have an anterior surface and a posterior surface. The anterior surface can comprise an aspheric surface. The anterior and posterior surfaces also can be shaped to provide average modulation transfer function (MTF) values that are between 0.1 and 0.4 at 100 lines per millimeter for at least 90% of the object vergences within the range of 0 to 2.5 Diopter (D) when the optic is inserted into the human eye having an aperture size of aperture size of 2 to 6 millimeters, 3 to 6 millimeters, or 4 to 6 millimeters (e.g., the aperture size can be 2 mm, 3 mm, 4 mm, 6 mm, any value within these ranges, or any range formed by such values). The average MTF values can comprise MTF values at 100 lines per millimeter integrated over the wavelengths between about 400 to 700 nm weighted by the photopic luminosity function for on axis objects.

In various embodiments, the human eye comprises a crystalline lens and the average modulation transfer function values are provided when the optic is inserted anterior of the crystalline lens. In various other embodiments, the human eye excludes a crystalline lens and the modulation transfer function values are provided when the optic is inserted in place of the crystalline lens. The lens further can comprise haptic portions. In addition, the optic can have an optical axis and a thickness through the optical axis that is between about 100-700 microns (or any range formed by any of the values in this range).

Certain embodiments described herein include a lens configured for implantation into an eye of a human. The lens can include an optic comprising transparent material. The optic can have an anterior surface and a posterior surface. The anterior surface can comprise an aspheric surface. The anterior and posterior surfaces also can be shaped to provide average modulation transfer function (MTF) values that are between 0.1 and 0.4 at 100 lines per millimeter for at least 90% of the object vergences within the range of 0 to 2.5 Diopter (D) when the optic is inserted into a model eye having an aperture size of 2 to 6 millimeters, 3 to 6 millimeters, or 4 to 6 millimeters (e.g., the aperture size can be 2 mm, 3 mm, 4 mm, 6 mm, any value within these ranges, or any range formed by such values). The average MTF values can comprise MTF values at 100 lines per millimeter integrated over the wavelengths between about 400 to 700 nm weighted by the photopic luminosity function for on axis objects.

The model eye can comprise a Liou-Brennan model eye. Alternatively, the model eye can comprise a Badal model eye. Furthermore, the model eye can comprise an Arizona model eye or an Indiana model eye. Other standardized or equivalent model eyes can be used.

In some embodiments, the modulation transfer function values can be provided when the optic is inserted in the model eye in a phakic configuration. In some other embodiments, the modulation transfer function values can be provided when the optic is inserted in the model eye in an aphakic configuration. The lens can further comprise haptic portions. Furthermore, the optic can have an optical axis and a thickness through the optical axis that is between about 100-700 microns (or any range formed by any of the values in this range).

Certain embodiments described herein include a lens configured for implantation into an eye of a human. The lens can include an optic comprising transparent material. The optic can have an anterior surface and a posterior surface and an exit pupil. The anterior surface can comprise an aspheric surface. The anterior and posterior surfaces can be shaped to provide a radial power profile characterized by $\Phi(r)=a+br^2+cr^4+dr^6+er^8$ for wavefront at the exit pupil of the optic for an object vergence of 0 to 2.5 Diopter (D) where r is the radial distance from an optical axis extending through the surface vertices on the anterior and posterior surfaces and a, b, c, d, and e are coefficients.

Certain embodiments described herein include a lens configured for implantation into an eye of a human. The lens can include an optic comprising transparent material. The lens can also include at least one haptic disposed with respect to the optic to affix the optic in the eye when implanted therein. The optic can include an anterior surface and a posterior surface. Each of the anterior surface and the posterior surface can have a surface vertex. The optic can have an optical axis through the surface vertices. The thickness along the optical axis can be between about 100-400 micrometers (or any range formed by any of the values in this range). In addition, at least one of the anterior and posterior surfaces can comprise aspheric surfaces. In some embodiments, the anterior surface can be convex. In addition, the posterior surface can be concave.

Certain embodiments described herein include a lens configured for implantation into an eye of a human. The lens can include an optic comprising transparent material. The lens can also include at least one haptic disposed with respect to the optic to affix the optic in the eye when implanted therein. The optic can include an anterior surface and a posterior surface. Each of the anterior surface and the posterior surface can have a surface vertex. The optic can have an optical axis through the surface vertices. At least one of the anterior and posterior surfaces can comprise an aspheric surface including perturbations comprising an aspheric higher order function of radial distance from the optical axis and at least one of the surfaces can have an aspheric shape that comprises a biconic. In some embodiments, the anterior surface can be convex. In addition, the posterior surface can be concave.

Certain embodiments described herein include a lens configured for implantation into an eye of a human. The lens can include an optic comprising transparent material. The lens can also include haptic portions disposed about the optic to affix the optic in the eye when implanted therein. The optic can include an anterior surface and a posterior surface. Each of the anterior surface and the posterior surface can have a surface vertex. The optic can have an optical axis through the surface vertices. The thickness along the optical axis can be between about 100-700 micrometers (or any range formed by any of the values in this range). In addition, the anterior and posterior surfaces can comprise aspheric surfaces.

Certain embodiments described herein include a lens configured for implantation into an eye of a human. The lens can include an optic comprising transparent material. The lens can also include at least one haptic disposed with respect to the optic to affix the optic in the eye when implanted therein. The optic can include an anterior surface and a posterior surface. Each of the anterior surface and the posterior surface can have a surface vertex. The optic can have an optical axis through the surface vertices. At least one of the anterior and posterior surfaces can comprise an aspheric surface that comprises a conic or biconic offset by perturbations comprising an aspheric higher order function of radial distance from the optical axis.

In various embodiments of the lens described herein comprising a transparent material, the transparent material can comprise collamer. The transparent can comprise silicone, acrylics, or hydrogels. The transparent material can comprise hydrophobic or hydrophilic material.

In various embodiments of the lens described herein, the anterior surface can be rotationally symmetric. The anterior surface can have a shape that includes a conic or biconic term. The anterior surface can have a shape that includes a conic or biconic term and aspheric higher order perturbation terms. In some embodiments of the lens, the posterior surface can have a shape that includes a conic or biconic term. The conic or biconic term can have a conic constant having a magnitude greater than zero. For example, the conic or biconic term can have a conic constant having a magnitude of at least one. As another example, the conic or biconic term can have a conic constant having a magnitude of at least ten.

In various embodiments of the lens described herein, the posterior surface can be rotationally non-symmetric. The posterior surface can have different curvature along different directions through the optical axis of the optic. For example, the posterior surface can have different curvature along orthogonal directions through the optical axis of the optic. The shape of the posterior surface can include a biconic term. The biconic term can have a conic constant having a magnitude greater than zero. For example, the biconic term can have a conic constant having a magnitude of at least one. As another example, the conic or biconic term can have a conic constant having a magnitude of at least ten. In various embodiments of the lens described herein, the optic can have a thickness along the optical axis of between 100-400 micrometers. For example, the thickness along the optical axis can be between 100-300 micrometers, between 100-200 micrometers, between 200-300 micrometers, between 300-400 micrometers, or any range formed by any of the values in these ranges.

In various embodiments of the lens described herein, the anterior and posterior surfaces of the lens can be shaped to provide average modulation transfer function (MTF) values that are between 0.1 and 0.4 at 100 lines per millimeter for at least 90% of the object vergences within the range of 0 to 2.5 Diopter (D) when the optic is inserted into a model eye having an aperture size of 2 to 6 millimeters, 3 to 6 millimeters, or 4 to 6 millimeters (e.g., the aperture size can be 2 mm, 3 mm, 4 mm, 6 mm, any value within these ranges, or any range formed by such values). The average MTF values can comprise MTF values at 100 lines per millimeter integrated over the wavelengths between about 400 to 700 nm weighted by the photopic luminosity function for on axis objects. The model eye can comprise a Liou-Brennan model eye, a Badal model eye, an Arizona model eye, an Indiana model eye, or any standardized or equivalent model eye.

In some such embodiments, the anterior and posterior surfaces of the lens are shaped to provide average modulation transfer function (MTF) values that are between 0.1 and 0.4 at 100 lines per millimeter for at least 95% or 98% of the object vergences within the range of 0 to 2.5 Diopter (D).

In various embodiments of the lens described herein, the anterior and posterior surfaces can be shaped to provide modulation transfer functions (MTF) without phase reversal for at least 90% of the object vergences within the range of 0 to 2.5 Diopter (D) when the optic is inserted into the model eye. In some such embodiments, the anterior and posterior surfaces are shaped to provide modulation transfer functions (MTF) without phase reversal for at least 95%, 98%, 99%, or 100% of the object vergences within the range of 0 to 2.5 Diopter (D) when said optic is inserted into the model eye.

In various embodiments of the lens described herein, the anterior surface can have a radius of curvature between 0 to 1 mm, between $1 \times 10^{-6}$ to $1 \times 10^{-3}$ mm, or between $5 \times 10^{-6}$ to $5 \times 10^{-4}$ mm. The anterior surface can have a conic constant between $-1 \times 10^6$ to $-100$ or between $-3 \times 10^5$ to $-2 \times 10^5$. The posterior surface can have a radius of curvature, $R_y$, between 0 to 20 mm. The posterior surface can have a radius of curvature, $R_x$, between 0 to 20 mm. The posterior surface can have a conic constant, $k_y$, between $-20$ to 20. The posterior surface can have a conic constant, $k_x$, between $-25$ to 0.

In some embodiments of the lens described herein, the lens can be configured to be disposed anterior to the natural lens of the eye. In some other embodiments of the lens, the lens can be configured to be disposed in the capsular bag.

Certain embodiments described herein include a method of implanting the lens of any of the embodiments of the lens. The method can include forming an opening in tissue of the eye and inserting the lens anterior of the natural lens of the eye. Certain embodiments described herein also include a method including forming an opening in tissue of the eye and inserting the lens in the capsular bag.

In various embodiments of the lens described herein, the optic can have a thickness along the optical axis that is between about 700 microns-4 millimeter. For example, the thickness along the optical axis can be between about 700 microns-3 millimeter, between about 700 microns-2 millimeter, between about 700 microns-1 millimeter, or any range formed by any of the values in these ranges.

Certain embodiments described herein include a lens pair configured for implantation into a pair of left and right eyes of a human. The lens pair includes a first lens. The first lens can include an optic comprising transparent material. The optic of the first lens can have an anterior surface and a posterior surface. The anterior surface can include an aspheric surface. The anterior and posterior surfaces of the first lens can be shaped to provide average modulation transfer function (MTF) values that are between 0.1 and 0.4 at 100 lines per millimeter for at least 90% of the object vergences within the range of 0 to 2.0 Diopter or 0 to 2.5 Diopter (D) when the optic of the first lens is inserted into a model eye having an aperture size of 2 to 6 millimeters, 3 to 6 millimeters, or 4 to 6 millimeters (e.g., the aperture size can be 2 mm, 3 mm, 4 mm, 6 mm, any value within these ranges, or any range formed by such values). The average MTF values of the first lens can comprise MTF values at 100 lines per millimeter integrated over the wavelengths between about 400 to 700 nm weighted by the photopic luminosity function for on axis objects.

The lens pair also includes a second lens. The second lens can include an optic comprising transparent material. The optic of the second lens can have an anterior surface and a posterior surface. The anterior surface can include an aspheric surface. The anterior and posterior surfaces of the second lens can be shaped to provide average modulation transfer function (MTF) values that are between 0.1 and 0.4 at 100 lines per millimeter for at least 90% of the object vergences within the range of $-2.0$ to 0 Diopter or $-2.5$ to 0 Diopter (D) when the optic of the second lens is inserted into a model eye having an aperture size of 2 to 6 millimeters, 3 to 6 millimeters, or 4 to 6 millimeters (e.g., the aperture size can be 2 mm, 3 mm, 4 mm, 6 mm, any value within these ranges, or any range formed by such values). The average MTF values of the second lens can comprise MTF values at 100 lines per millimeter integrated over the wavelengths between about 400 to 700 nm weighted by the photopic luminosity function for on axis objects.

The model eye can comprise a Liou-Brennan model eye. Alternatively, the model eye can comprise a Badal model eye. Furthermore, the model eye can comprise an Arizona model eye or an Indiana model eye. Other standardized or equivalent model eyes can be used.

In various embodiments of the lens pair, the modulation transfer function values of the first or second lens can be provided when the optic of the first or second lens is inserted in the model eye in a phakic configuration. In various other embodiments, the modulation transfer function values of the first or second lens can be provided when the optic of the first or second lens is inserted in the model eye in an aphakic configuration.

In various embodiments of the lens pair, the first or second lens can further comprise haptic portions. The optic of the first or second lens can have an optical axis and a thickness through the optical axis that is between about 100-700 microns. In other embodiments, the optic of the first or second lens can have an optical axis and a thickness through the optical axis that is between about 700 microns-4 millimeter. In some such embodiments, the thickness along the optical axis can be between about 700 microns-3 millimeter, between about 700 microns-2 millimeter, between about 700 microns-1 millimeter, or any range formed by any of the values in these ranges.

In various embodiments of the lens pair, the anterior and posterior surfaces of the first lens can be shaped to provide average modulation transfer function (MTF) values that are between 0.1 and 0.4 at 100 lines per millimeter for at least 95% or 98% of the object vergences within the range of 0 to 2.5 Diopter (D).

In various embodiments of the lens pair, the anterior and posterior surfaces of the second lens can be shaped to provide average modulation transfer function (MTF) values that are between 0.1 and 0.4 at 100 lines per millimeter for at least 95% or 98% of the object vergences within the range of −2.5 to 0 Diopter (D).

In various embodiments of the lens pair, the anterior and posterior surfaces of the first lens can shaped to provide modulation transfer functions (MTF) without phase reversal for at least 90%, 95%, 98%, 99%, or 100% of the object vergences within the range of 0 to 2.5 Diopter (D) when said optic is inserted into the model eye.

In various embodiments of the lens pair, the anterior and posterior surfaces of the second lens can be shaped to provide modulation transfer functions (MTF) without phase reversal for at least 90%, 95%, 98%, 99%, or 100% of the object vergences within the range of −2.5 to 0 Diopter (D) when said optic is inserted into the model eye.

Certain embodiments described herein include a lens configured for implantation into an eye of a human. The lens can include an optic comprising transparent material. The optic can have an anterior surface and a posterior surface. Each of the anterior surface and the posterior surface can have a surface vertex. The optic can have an optical axis through the surface vertices. At least one of the anterior and posterior surfaces can comprise a surface having a first portion and a second portion. The first portion can be disposed centrally about the optical axis. The second portion can surround the first portion and can have a different surface profile than the first portion. The first portion can be configured to provide an extended depth of field. The second portion can be configured to provide an enhanced vision quality metric at distance in comparison to the first portion.

In some such embodiments, distance can comprise objects between infinity to 2 meters or distance can comprises 0 D vergence. In various embodiments of the lens, the lens can further comprise a third portion surrounding the second portion. The third portion can have a different surface profile than the second portion. In some embodiments, the third portion can have a similar surface profile as the first portion. The second portion can be configured to provide an enhanced vision quality metric at distance in comparison to the third portion. For example, the enhanced vision quality metric can be a modulation transfer function, a contrast sensitivity, a derivation thereof, or a combination thereof. In some embodiments, the first portion can have a shape that comprises a conic, biconic, or biaspheric envelope offset by perturbations of the envelope comprising an aspheric higher order function of radial distance from the optical axis.

Certain embodiments described herein include a lens configured for implantation into an eye of a human. The lens can include an optic comprising transparent material. The optic can have an anterior surface and a posterior surface. Each of the anterior surface and the posterior surface can have a surface vertex. The optic can have an optical axis through the surface vertices. At least one of the anterior and posterior surfaces can comprise a surface having a first portion and a second portion. The first portion can have a shape that comprises a conic, biconic, or biaspheric envelope offset by perturbations with respect to the envelope comprising an aspheric higher order function of radial distance from the optical axis. The second portion can have a shape that comprises a conic, biconic, or biaspheric envelope not offset by perturbations of the envelope comprising an aspheric higher order function of radial distance from the optical axis.

In various embodiments of the lens, the first portion can be disposed centrally about the optical axis. The second portion can surround said first portion. In some embodiments, the lens can include a third portion surrounding the second portion. The third portion can have a shape that comprises a conic, biconic, or biaspheric envelope offset by perturbations with respect to the envelope comprising an aspheric higher order function of radial distance from the optical axis. In some such embodiments, the third portion can have substantially the same conic, biconic, or biaspheric envelope offset by perturbations with respect to the envelope comprising an aspheric higher order function of radial distance from the optical axis as the first portion.

Certain embodiments described herein include a lens configured for implantation into an eye of a human. The lens can include an optic comprising transparent material. The optic can have an anterior surface and a posterior surface. Each of the anterior surface and the posterior surface can have a surface vertex. The optic can have an optical axis through the surface vertices. At least one of the anterior and posterior surfaces can comprise a surface having a first portion and a second portion. The first portion can be disposed centrally about the optical axis. The second portion can surround the first portion. The first portion can have higher spherical aberration control that provides extended depth of field than the second portion.

In various embodiments, the lens can include a third portion surrounding the second portion. The third portion can have higher spherical aberration control that provides extended depth of field than the second portion. The third portion can have substantially the same spherical aberration control as the first portion. The first portion can have a shape that comprises a conic, biconic, or biaspheric envelope offset by perturbations from the envelope comprising an aspheric higher order function of radial distance from the optical axis.

In various embodiments of the lens having a third portion, the third portion can have a shape that comprises a conic, biconic, or biaspheric envelope offset by perturbations from the envelope comprising an aspheric higher order function of radial distance from the optical axis.

In various embodiments of the lens having a shape that comprises a conic, biconic, or biaspheric envelope offset by perturbations from the envelope comprising an aspheric higher order function of radial distance from the optical axis, the aspheric higher order function can include at least one even order term, $a_{2n}r^{2n}$, where n is an integer and $a_{2n}$ is a coefficient and r is the radial distance from the optical axis. For example, the aspheric higher order function can include a second order term, $a_2r^2$, where $a_2$ is a coefficient and r is the radial distance from the optical axis. As another example, the aspheric higher order function can include a fourth order term, $a_4r^4$, where $a_4$ is a coefficient and r is the radial distance from the optical axis. The aspheric higher order function can also include a sixth order term, $a_6r^6$ where $a_6$ is a coefficient and r is the radial distance from the optical axis. Further, the aspheric higher order function can include an eighth order term, $a_8r^8$ where $a_8$ is a coefficient and r is the radial distance from the optical axis.

In various embodiments of the lens having a first and second portion, the lens can further comprise a transition portion providing a smooth transition without discontinuity between the first and second portions. The transition portion can have a distance between inner and outer radii in the range of about 0.1-1 mm. The first portion can have a maximum cross-sectional diameter in the range of about 2.5-4.5 mm. For example, the first portion can have a maximum cross-sectional diameter of about 3.75 mm. The second portion can have a distance between inner and outer radii in the range of about 1-3.5 mm. In some embodiments, the second portion can have a distance between inner and outer radii in the range of about 0.25-1.5 mm.

In various embodiments of the lens, the optic can have a thickness along the optical axis that is in the range of about 100-700 microns (or any range formed by any of the values in this range). Alternatively, the optic can have a thickness along the optical axis that is in the range of about 700 microns to 4 millimeters (or any range formed by any of the values in this range). In various embodiments, the lens can also include at least one haptic disposed with respect to the optic to affix the optic in the eye when implanted therein. In some embodiments, the anterior surface can comprise the surface having the first and second portions. The posterior surface can comprise a shape having a biconic envelope.

Certain embodiments described herein include a lens configured for implantation into an eye of a human. The lens can include an optic comprising transparent material. The optic can have an anterior surface and a posterior surface. Each of the anterior surface and the posterior surface can have a surface vertex. The optic can have an optical axis through the surface vertices. At least one of the anterior and posterior surfaces can comprise a surface having a first portion and a second portion. The first portion can be disposed centrally about the optical axis. The second portion can surround the first portion. The first portion can be configured to provide an extended depth of field. The second portion can be configured to provide a monofocal distance focusing.

In some such embodiments, the lens can further comprise a third portion surrounding the second portion. The third portion can be configured to provide an extended depth of field. The first portion can have a shape that comprises a conic, biconic, or biaspheric envelope offset by perturbations with respect to the envelope comprising an aspheric higher order function of radial distance from the optical axis. In addition, the third portion can have a shape that comprises a conic, biconic, or biaspheric envelope offset by perturbations with respect to the envelope comprising an aspheric higher order function of radial distance from the optical axis.

In various embodiments of the lens having first and second portions, each of the first and second portions can have a caustic. The second portion can have a conic constant such that the caustic of the second portion blends smoothly with the caustic of the first portion. In some examples, the caustic of the second portion blends more smoothly with the caustic of the first portion than if the second portion comprises a spherical surface. In various embodiments of the lens having a third portion, the second and third portions can have a caustic. The second portion can have a conic constant such that the caustic of the second portion blends smoothly with the caustic of the third portion. In some examples, the caustic of the second portion blends more smoothly with the caustic of the third portion than if the second portion comprises a spherical surface.

In certain embodiments of the lens having first and second portions, the anterior surface can be convex. The posterior surface can be concave. For example, the anterior surface can be convex and the posterior surface can be concave such that the optic is meniscus shaped. In various other embodiments, the posterior surface can be convex. In some embodiments, the anterior surface can be concave. In addition, in various embodiments of the lens having first and second portions, the second portion can have a shape that comprises a conic, biconic, or biaspheric envelope not offset by perturbations of the envelope comprising an aspheric higher order function of radial distance from the optical axis.

Certain embodiments described herein include a lens configured for implantation into an eye of a human. The lens can include an optic comprising transparent material. The optic can have an anterior surface and a posterior surface. Each of the anterior surface and the posterior surface can have a surface vertex. The optic can have an optical axis through the surface vertices. The lens can include at least one haptic disposed with respect to the optic to affix the optic in the eye when implanted therein. The anterior and posterior surfaces can comprise aspheric surfaces and the posterior surface can have an aspheric shape that comprises a biconic offset by perturbations comprising an aspheric higher order function of radial distance from the optical axis. The posterior surface can have an absolute value of ratio $R_x/R_y$ between 0, 0.1, 0.2, 0.25, or 0.5 and 100 and an absolute value of ratio $k_x/k_y$ between 0, 0.1, 0.2, 0.25, or 0.5 and 100. In some embodiments, the absolute value of the ratio $R_x/R_y$ is between 0, 0.1, 0.2, 0.25, or 0.5 and 75; 0, 0.1, 0.2, 0.25, or 0.5 and 50; 0, 0.1, 0.2, 0.25, or 0.5 and 25; or 0, 0.1, 0.2, 0.25, or 0.5 and 10. In addition, in some embodiments, the absolute value of the ratio $k_x/k_y$ is between 0, 0.1, 0.2, 0.25, or 0.5 and 75; 0, 0.1, 0.2, 0.25, or 0.5 and 50; 0, 0.1, 0.2, 0.25, or 0.5 and 25; or 0, 0.1, 0.2, 0.25, or 0.5 and 10.

Certain embodiments described herein include a lens configured for implantation into an eye of a human. The lens can include an optic comprising transparent material. The optic can have an anterior surface and a posterior surface. The anterior surface or posterior surface can comprise an aspheric surface. The anterior and posterior surfaces can be shaped to provide a Salvador Image Quality (SIQ) metric that is at least 0.6, 0.7, 0.8, 0.9, or 1 for at least 90%, 95%, or 98% of the object vergences within the range of 0 to +1.5 D, 0 to +2.0 D, or 0 to +2.5 D when the optic is inserted into the human eye having an aperture size of 4 to 6 millimeters. For example, the aperture size can be 6 mm.

Certain embodiments described herein include a lens configured for implantation into an eye of a human. The lens can include an optic comprising transparent material. The optic can have an anterior surface and a posterior surface. The anterior surface or posterior surface can comprise an aspheric surface. The anterior and posterior surfaces can be shaped to provide an above average psychophysical grade for at least 90%, 95%, or 98% of the object vergences within the range of 0 to +1.5 D, 0 to +2.0 D, or 0 to +2.5 D when the optic is inserted into the human eye having an aperture size of 4 to 6 millimeters or into a model eye having an aperture size of 4 to 6 millimeters. In some such embodiment, each of the anterior surface and the posterior surface can have a surface vertex. The optic can have an optical axis through the surface vertices. The anterior or posterior surface can have an aspheric shape that comprises a biconic offset by perturbations comprising an aspheric higher order function of radial distance from the optical axis.

In various embodiments, the optic can comprise an exit pupil, and the anterior and posterior surfaces can be shaped to provide a radial power profile characterized by $\Phi(r)=a+$ $br^2+cr^4+dr^6+er^8$ for wavefront at the exit pupil of the optic for an object vergence of 0 to 2.5 D where r is the radial distance from the optical axis and a, b, c, d, and e are coefficients. In some embodiments, a thickness along the optical axis can be between about 100-700 micrometers. The anterior surface can be convex and the posterior surface can be concave such that the optic is meniscus shaped.

EXAMPLES

1. A lens configured for implantation into an eye of a human, said lens comprising:
an optic comprising transparent material, said optic having an anterior surface and a posterior surface, said anterior surface being convex and said posterior surface being concave such that said optic is meniscus shaped, each of said convex anterior surface and said concave posterior surface having a surface vertex, said optic having an optical axis through said surface vertices and a thickness along said optical axis that is between about 100-700 micrometers,
haptic portions disposed about the optic to affix the optic in the eye when implanted therein,
wherein said anterior and posterior surfaces comprise aspheric surfaces.

2. The lens of Example 1, wherein said anterior surface is rotationally symmetric.

3. The lens of Example 1, wherein said anterior surface has a shape that includes a conic or biconic term.

4. The lens of Example 3, wherein said anterior surface has a shape that includes a conic or biconic term and aspheric higher order perturbation terms.

5. The lens of Example 2, wherein said posterior surface has a shape that includes a conic or biconic term.

6. The lens of Example 5, wherein said conic or biconic term has a conic constant having a magnitude greater than zero.

7. The lens of Example 6, wherein said conic or biconic term has a conic constant having a magnitude of at least one.

8. The lens of Example 7, wherein said conic or biconic term has a conic constant having a magnitude of at least ten.

9. The lens of any of Examples 2-4, wherein said posterior surface is rotationally non-symmetric and has different curvature along different directions through said optical axis of said optic.

10. The lens of Example 9, wherein said posterior surface has different curvature along orthogonal directions through said optical axis of said optic.

11. The lens of any of Examples 2-3, wherein said posterior surface is rotationally non-symmetric and has a shape that includes a biconic term.

12. The lens of Example 11, wherein said biconic term has a conic constant having a magnitude greater than zero.

13. The lens of Example 12, wherein said biconic term has a conic constant having a magnitude of at least one.

14. The lens of Example 13, wherein said biconic term has a conic constant having a magnitude of at least ten.

15. A lens configured for implantation into an eye of a human, said lens comprising:
an optic comprising transparent material, said optic having an anterior surface and a posterior surface, said anterior surface being convex and said posterior surface being concave such that said optic is meniscus shaped, each of said convex anterior surface and said concave posterior surface having a surface vertex, said optic having an optical axis through said surface vertices,
at least one haptic disposed with respect to the optic to affix the optic in the eye when implanted therein,
wherein said anterior and posterior surfaces comprise aspheric surfaces and said anterior surface has an aspheric shape that comprises a conic or biconic offset by perturbations comprising an aspheric higher order function of radial distance from the optical axis.

16. The lens of Example 15, wherein said aspheric higher order function includes a second order term, $a_2 r^2$, where $a_2$ is a coefficient and r is the radial distance from the optical axis.

17. The lens of Example 15 or 16, wherein said aspheric higher order function includes a fourth order term, $a_4 r^4$, where $a_4$ is a coefficient and r is the radial distance from the optical axis.

18. The lens of any of Examples 15-17, wherein said aspheric higher order function includes a sixth order term, $a_6 r^6$ where $a_6$ is a coefficient and r is the radial distance from the optical axis.

19. The lens of any of Examples 15-18, wherein said aspheric higher order function includes an eighth order term, $a_8 r^8$ where $a_8$ is a coefficient and r is the radial distance from the optical axis.

20. The lens of Example 15, wherein said aspheric higher order function includes at least one even order term, $a_{2n} r^{2n}$, where n is an integer and $a_{2n}$ is a coefficient and r is the radial distance from the optical axis.

21. The lens of any of Examples 15-20, comprising a plurality of haptics.

22. The lens of any of Examples 15-21, wherein said optic has a thickness along said optical axis that is between about 100-700 microns.

23. The lens of any of Examples 15-22, wherein said anterior surface has an aspheric shape that comprises a biconic offset by said perturbations.

24. A lens configured for implantation into an eye of a human, said lens comprising:
an optic comprising transparent material, said optic having an anterior surface and a posterior surface, said anterior surface comprising an aspheric surface,
wherein the anterior and posterior surfaces are shaped to provide average modulation transfer function (MTF) values that are between 0.1 and 0.4 at 100 lines per millimeter for at least 90% of the object vergences within the range of 0 to 2.5 Diopter (D) when said optic is inserted into said human eye having an aperture size of 4 to 6 millimeters, wherein said average MTF values comprise MTF values at 100 lines per millimeter integrated over the wavelengths between about 400 to 700 nm weighted by the photopic luminosity function for on axis objects.

25. The lens of Example 24, wherein said human eye comprises a crystalline lens and said average modulation transfer function values are provided when said optic is inserted anterior of said crystalline lens.

26. The lens of Example 24, wherein said human eye excludes a crystalline lens and said modulation transfer function values are provided when said optic is inserted in place of the crystalline lens.

27. The lens of any of Examples 24-26, further comprising haptic portions.

28. The lens of any of Examples 24-27, wherein said optic has an optical axis and a thickness through said optical axis that is between about 100-700 microns.

29. A lens configured for implantation into an eye of a human, said lens comprising:

an optic comprising transparent material, said optic having an anterior surface and a posterior surface, said anterior surface comprising an aspheric surface, wherein the anterior and posterior surfaces are shaped to provide average modulation transfer function (MTF) values that are between 0.1 and 0.4 at 100 lines per millimeter for at least 90% of the object vergences within the range of 0 to 2.5 Diopter (D) when said optic is inserted into a model eye having an aperture size of 4 to 6 millimeters, wherein said average MTF values comprise MTF values at 100 lines per millimeter integrated over the wavelengths between about 400 to 700 nm weighted by the photopic luminosity function for on axis objects.

30. The lens of Example 29, wherein said model eye comprises a Liou-Brennan model eye.

31. The lens of Example 29, wherein said model eye comprises a Badal model eye.

32. The lens of Example 29, wherein said model eye comprises an Arizona model eye or an Indiana model eye.

33. The lens of any of Examples 29-32, wherein said modulation transfer function values are provided when said optic is inserted in said model eye in a phakic configuration.

34. The lens of any of Examples 29-32, wherein said modulation transfer function values are provided when said optic is inserted in said model eye in an aphakic configuration.

35. The lens of any of Examples 29-34, further comprising haptic portions.

36. The lens of any of Examples 29-35, wherein said optic has an optical axis and a thickness through said optical axis that is between about 100-700 microns.

37. The lens of any of Examples 29-36, wherein said aperture size is 6 millimeters.

38. The lens of any of Examples 29-26, wherein said aperture size is 4 millimeters.

39. A lens configured for implantation into an eye of a human, said lens comprising:

an optic comprising transparent material, said optic having an anterior surface and a posterior surface and an exit pupil, said anterior surface comprising an aspheric surface, wherein the anterior and posterior surfaces are shaped to provide a radial power profile characterized by $\Phi(r) = a+br^2+cr^4+dr^6+er^8$ for wavefront at the exit pupil of the optic for an object vergence of 0 to 2.5 Diopter (D) where r is the radial distance from an optical axis extending through the surface vertices on the anterior and posterior surfaces and a, b, c, d, and e are coefficients.

40. A lens configured for implantation into an eye of a human, said lens comprising:

an optic comprising transparent material, said optic having an anterior surface and a posterior surface, said anterior surface being convex and said posterior surface being concave such that said optic is meniscus shaped, each of said convex anterior surface and said concave posterior surface having a surface vertex, said optic having an optical axis through said surface vertices, at least one haptic disposed with respect to optic to affix the optic in the eye when implanted therein, wherein said anterior and posterior surfaces comprise aspheric surfaces and said posterior surface has an aspheric shape that comprises a conic or biconic offset by perturbations comprising an aspheric higher order function of radial distance from the optical axis.

41. The lens of Example 40, wherein said aspheric higher order function includes a second order term, $a_2 r^2$, where $a_2$ is a coefficient and r is the radial distance from the optical axis.

42. The lens of Example 40 or 41, wherein said aspheric higher order function includes a fourth order term, $a_4 r^4$, where $a_4$ is a coefficient and r is the radial distance from the optical axis.

43. The lens of any of Examples 40-42, wherein said aspheric higher order function includes a sixth order term, $a_6 r^6$ where $a_6$ is a coefficient and r is the radial distance from the optical axis.

44. The lens of any of Examples 40-43, wherein said aspheric higher order function includes an eighth order term, $a_8 r^8$ where $a_8$ is a coefficient and r is the radial distance from the optical axis.

45. The lens of Example 40, wherein said aspheric higher order function includes at least one even order term, $a_{2n} r^{2n}$, where n is an integer and $a_{2n}$ is a coefficient and r is the radial distance from the optical axis.

46. The lens of any of Examples 40-45, wherein said optic has a thickness along said optical axis that is between about 100-700 microns.

47. The lens of any of Examples 40-46, wherein said posterior surface has an aspheric shape that comprises a biconic offset by said perturbations.

48. A lens pair configured for implantation into a pair of left and right eyes of a human, comprising:

a first lens comprising:
an optic comprising transparent material, said optic of said first lens having an anterior surface and a posterior surface, said anterior surface comprising an aspheric surface,
wherein the anterior and posterior surfaces of said first lens are shaped to provide average modulation transfer function (MTF) values that are between 0.1 and 0.4 at 100 lines per millimeter for at least 90% of the object vergences within the range of 0 to 2.5 Diopter (D) when said optic of said first lens is inserted into a model eye having an aperture size of 4 to 6 millimeters, wherein said average MTF values of said first lens comprise MTF values at 100 lines per millimeter integrated over the wavelengths between about 400 to 700 nm weighted by the photopic luminosity function for on axis objects, and a second lens comprising:
an optic comprising transparent material, said optic of said second lens having an anterior surface and a posterior surface, said anterior surface comprising an aspheric surface,
wherein the anterior and posterior surfaces of said second lens are shaped to provide average modulation transfer function (MTF) values that are between 0.1 and 0.4 at 100 lines per millimeter for at least 90% of the object vergences within the range of −2.5 to 0 Diopter (D) when said optic of said second lens is inserted into the model eye having an aperture size of 4 to 6 millimeters, wherein said average MTF values of said second lens comprise MTF values at 100 lines per millimeter integrated over the wavelengths between about 400 to 700 nm weighted by the photopic luminosity function for on axis objects.

49. The lens pair of Example 48, wherein said model eye comprises a Liou-Brennan model eye.

50. The lens pair of Example 48, wherein said model eye comprises a Badal model eye.

51. The lens pair of Example 48, wherein said model eye comprises an Arizona model eye or an Indiana model eye.

52. A lens configured for implantation into an eye of a human, said lens comprising:
an optic comprising transparent material, said optic having an anterior surface and a posterior surface, each of said anterior surface and said posterior surface having a surface vertex, said optic having an optical axis through said surface vertices and a thickness at said along said optical axis that is between about 100-400 micrometers,
at least one haptic disposed with respect to the optic to affix the optic in the eye when implanted therein,
wherein at least one of said anterior and posterior surfaces comprise aspheric surfaces.

53. The lens of Example 52, wherein said anterior surface is convex.

54. The lens of Example 52 or 53, wherein said posterior surface is concave.

55. A lens configured for implantation into an eye of a human, said lens comprising:
an optic comprising transparent material, said optic having an anterior surface and a posterior surface, each of said anterior surface and said posterior surface having a surface vertex, said optic having an optical axis through said surface vertices,
at least one haptic disposed with respect to the optic to affix the optic in the eye when implanted therein,
wherein at least one of said anterior and posterior surfaces comprise an aspheric surface including perturbations comprising an aspheric higher order function of radial distance from the optical axis and at least one of said surfaces has an aspheric shape that comprises a biconic.

56. The lens of Example 55, wherein said anterior surface is convex.

57. The lens of Example 55 or 56, wherein said posterior surface is concave.

58. A lens configured for implantation into an eye of a human, said lens comprising:
an optic comprising transparent material, said optic having an anterior surface and a posterior surface, each of said anterior surface and said posterior surface having a surface vertex, said optic having an optical axis through said surface vertices and a thickness at said along said optical axis that is between about 100-700 micrometers,
haptic portions disposed about the optic to affix the optic in the eye when implanted therein,
wherein said anterior and posterior surfaces comprise aspheric surfaces.

59. A lens configured for implantation into an eye of a human, said lens comprising:
an optic comprising transparent material, said optic having an anterior surface and a posterior surface, each of said anterior surface and said posterior surface having a surface vertex, said optic having an optical axis through said surface vertices,
at least one haptic disposed with respect to the optic to affix the optic in the eye when implanted therein,
wherein at least one of said anterior and posterior surfaces comprise an aspheric surface that comprises a conic or biconic offset by perturbations comprising an aspheric higher order function of radial distance from the optical axis.

60. The lens of any of Examples 1-47 or any of Examples 52-59, wherein said transparent material comprises collamer.

61. The lens of any of Examples 1-47 or any of Examples 52-59, wherein said transparent material comprises silicone, acrylic, or hydrogel.

62. The lens of any of Examples 1-47 or any of Examples 52-59, wherein said transparent material comprises hydrophobic or hydrophilic material.

63. The lens of any of Examples 1-23, 28, 36, any of Examples 39-47, or any of Examples 55-59, wherein said optic has a thickness along said optical axis of between 100-400 micrometers.

64. The lens of Example 63, wherein said optic has a thickness along said optical axis of between 100-300 micrometers.

65. The lens of Example 64, wherein said optic has a thickness along said optical axis of between 100-200 micrometers.

66. The lens of Example 64, wherein said optic has a thickness along said optical axis of between 200-300 micrometers.

67. The lens of Example 63, wherein said optic has a thickness along said optical axis of between 300-400 micrometers.

68. The lens of any of Examples 1-28, any of Examples 39-47, or any of Examples 52-59, wherein the anterior and posterior surfaces of said optic are shaped to provide average modulation transfer function (MTF) values that are between 0.1 and 0.4 at 100 lines per millimeter for at least 90% of the object vergences within the range of 0 to 2.5 Diopter (D) when said optic is inserted into a model eye having an aperture size of 4 to 6 millimeters, wherein said average MTF values comprise MTF values at 100 lines per millimeter integrated over the wavelengths between about 400 to 700 nm weighted by the photopic luminosity function for on axis objects.

69. The lens of Example 68, wherein said model eye comprises a Liou-Brennan model eye.

70. The lens of Example 68, wherein said model eye comprises a Badal model eye.

71. The lens of Example 68, wherein said model eye comprises an Arizona model eye or an Indiana model eye.

72. The lens of any of Examples 24-38 or any of Examples 68-71, wherein the anterior and posterior surfaces of said optic are shaped to provide average modulation transfer function (MTF) values that are between 0.1 and 0.4 at 100 lines per millimeter for at least 95% of the object vergences within the range of 0 to 2.5 Diopter (D).

73. The lens of Example 72, wherein the anterior and posterior surfaces of said optic are shaped to provide average modulation transfer function (MTF) values that are between 0.1 and 0.4 at 100 lines per millimeter for at least 98% of the object vergences within the range of 0 to 2.5 Diopter (D).

74. The lens of any of Examples 1-47 or any of Examples 52-73, wherein anterior and posterior surfaces are shaped to provide modulation transfer functions (MTF) without phase reversal for at least 90% of the object vergences within the range of 0 to 2.5 Diopter (D) when said optic is inserted into a model eye having an aperture size of 4 to 6 millimeters.

75. The lens of Example 74, wherein anterior and posterior surfaces are shaped to provide modulation transfer functions (MTF) without phase reversal for at least 95% of the object vergences within the range of 0 to 2.5 Diopter (D) when said optic is inserted into a model eye having an aperture size of 4 to 6 millimeters.

76. The lens of Example 75, wherein anterior and posterior surfaces are shaped to provide modulation transfer functions (MTF) without phase reversal for at least 98% of the object vergences within the range of 0 to 2.5 Diopter (D) when said optic is inserted into a model eye having an aperture size of 4 to 6 millimeters.

77. The lens of Example 76, wherein anterior and posterior surfaces are shaped to provide modulation transfer functions (MTF) without phase reversal for at least 99% of the object vergences within the range of 0 to 2.5 Diopter (D) when said optic is inserted into a model eye having an aperture size of 4 to 6 millimeters.

78. The lens of Example 77, wherein anterior and posterior surfaces are shaped to provide modulation transfer functions (MTF) without phase reversal for at least 100% of the object vergences within the range of 0 to 2.5 Diopter (D) when said optic is inserted into a model eye having an aperture size of 4 to 6 millimeters.

79. The lens of any of Examples 1-47 or any of Examples 52-78, wherein the anterior surface has a radius of curvature between 0 to 1 mm.

80. The lens of any of Examples 1-47 or any of Examples 52-78, wherein the anterior surface has a radius of curvature between $1 \times 10^{-6}$ to $1 \times 10^{-3}$ mm.

81. The lens of any of Examples 1-47 or any of Examples 52-78, wherein the anterior surface has a radius of curvature between $5 \times 10^{-6}$ to $5 \times 10^{-4}$ mm.

82. The lens of any of Examples 1-47 or any of Examples 52-81, wherein the anterior surface has a conic constant between $-1 \times 10^6$ to $-100$.

83. The lens of any of Examples 1-47 or any of Examples 52-81, wherein the anterior surface has a conic constant between $-3 \times 10^5$ to $-2 \times 10^5$.

84. The lens of any of Examples 1-47 or any of Examples 52-83, wherein the posterior surface has a radius of curvature, $R_y$, between 0 to 20 mm.

85. The lens of any of Examples 1-47 or any of Examples 52-84, wherein the posterior surface has a radius of curvature, $R_x$, between 0 to 20 mm.

86. The lens of any of Examples 1-47 or any of Examples 52-85, wherein the posterior surface has a conic constant, $k_y$, between −20 to 20.

87. The lens of any of Examples 1-47 or any of Examples 52-86, wherein the posterior surface has a conic constant, $k_x$, between −25 to 0.

88. A method of implanting the lens of any of Examples 1-47 or any of Examples 52-87, comprising:
forming an opening in tissue of the eye;
inserting the lens anterior of the natural lens of the eye.

89. A method of implanting the lens of any of Examples 1-47 or any of Examples 52-87, comprising:
forming an opening in tissue of the eye;
inserting the lens in the capsular bag.

90. The lens of any of Examples 1-47 or any of Examples 52-87 configured to be disposed anterior of the natural lens of the eye.

91. The lens of any of Examples 1-47 or any of Examples 52-87 configured to be disposed in the capsular bag.

92. The lens of any of Examples 15-21, any of Examples 39-45, any of Examples 55-57, or Example 59, wherein said optic has a thickness along said optical axis that is between about 700 microns-4 millimeter.

93. The lens of Example 24 or any of Examples 29-32, wherein said optic has an optical axis and a thickness along said optical axis that is between about 700 microns-4 millimeter.

94. The lens of Example 92 or 93, wherein said optic has a thickness along said optical axis that is between about 700 microns-3 millimeter.

95. The lens of Example 94, wherein said optic has a thickness along said optical axis that is between about 700 microns-2 millimeter.

96. The lens of Example 95, wherein said optic has a thickness along said optical axis that is between about 700 microns-1 millimeter.

97. The lens pair of any of Examples 48-51, wherein said modulation transfer function values of said first or second lens are provided when said optic of said first or second lens is inserted in said model eye in a phakic configuration.

98. The lens pair any of Examples 48-51, wherein said modulation transfer function values of said first or second lens are provided when said optic of said first or second lens is inserted in said model eye in an aphakic configuration.

99. The lens pair of any of Examples 48-51 or any of Examples 97-98, wherein the first or second lens further comprises haptic portions.

100. The lens pair of any of Examples 48-51 or any of Examples 97-99, wherein said optic of said first or second lens has an optical axis and a thickness through said optical axis that is between about 100-700 microns.

101. The lens pair of any of Examples 48-51, wherein said optic of said first or second lens has an optical axis and a thickness through said optical axis that is between about 700 microns-4 millimeter.

102. The lens pair of Example 101, wherein said optic of said first or second lens has a thickness along said optical axis that is between about 700 microns-3 millimeter.

103. The lens pair of Example 102, wherein said optic of said first or second lens has a thickness along said optical axis that is between about 700 microns-2 millimeter.

104. The lens pair of Example 103, wherein said optic of said first or second lens has a thickness along said optical axis that is between about 700 microns-1 millimeter.

105. The lens pair of any of Examples 48-51 or any of Examples 97-104, wherein said aperture size is 6 millimeters.

106. The lens pair of any of Examples 48-51 or any of Examples 97-104, wherein said aperture size is 4 millimeters.

107. The lens pair of any of Examples 48-51 or any of Examples 97-106, wherein the anterior and posterior surfaces of said first lens are shaped to provide average modulation transfer function (MTF) values that are between 0.1 and 0.4 at 100 lines per millimeter for at least 95% of the object vergences within the range of 0 to 2.5 Diopter (D).

108. The lens pair of Example 107, wherein the anterior and posterior surfaces of said first lens are shaped to provide average modulation transfer function (MTF) values that are between 0.1 and 0.4 at 100 lines per millimeter for at least 98% of the object vergences within the range of 0 to 2.5 Diopter (D).

109. The lens pair of any of Examples 48-51 or any of Examples 97-108, wherein the anterior and posterior surfaces of said second lens are shaped to provide average modulation transfer function (MTF) values that are between 0.1 and 0.4 at 100 lines per millimeter for at least 95% of the object vergences within the range of −2.5 to 0 Diopter (D).

110. The lens pair of Example 109, wherein the anterior and posterior surfaces of said second lens are shaped to provide average modulation transfer function (MTF) values that are between 0.1 and 0.4 at 100 lines per millimeter for at least 98% of the object vergences within the range of −2.5 to 0 Diopter (D).

111. The lens pair of any of Examples 48-51 or any of Examples 97-110, wherein anterior and posterior surfaces of said first lens are shaped to provide modulation transfer functions (MTF) without phase reversal for at least 90% of the object vergences within the range of 0 to 2.5 Diopter (D) when said optic is inserted into the model eye having an aperture size of 4 to 6 millimeters.

112. The lens pair of Example 111, wherein anterior and posterior surfaces of said first lens are shaped to provide modulation transfer functions (MTF) without phase reversal for at least 95% of the object vergences within the range of 0 to 2.5 Diopter (D) when said optic is inserted into the model eye having an aperture size of 4 to 6 millimeters.

113. The lens pair of Example 112, wherein anterior and posterior surfaces of said first lens are shaped to provide modulation transfer functions (MTF) without phase reversal for at least 98% of the object vergences within the range of 0 to 2.5 Diopter (D) when said optic is inserted into the model eye having an aperture size of 4 to 6 millimeters.

114. The lens pair of Example 113, wherein anterior and posterior surfaces of said first lens are shaped to provide modulation transfer functions (MTF) without phase reversal for at least 99% of the object vergences within the range of 0 to 2.5 Diopter (D) when said optic is inserted into the model eye having an aperture size of 4 to 6 millimeters.

115. The lens pair of Example 114, wherein anterior and posterior surfaces of said first lens are shaped to provide modulation transfer functions (MTF) without phase reversal for 100% of the object vergences within the range of 0 to 2.5 Diopter (D) when said optic is inserted into the model eye having an aperture size of 4 to 6 millimeters.

116. The lens pair of any of Examples 48-51 or any of Examples 97-115, wherein anterior and posterior surfaces of said second lens are shaped to provide modulation transfer functions (MTF) without phase reversal for at least 90% of the object vergences within the range of −2.5 to 0 Diopter (D) when said optic is inserted into the model eye having an aperture size of 4 to 6 millimeters.

117. The lens pair of Example 116, wherein anterior and posterior surfaces of said second lens are shaped to provide modulation transfer functions (MTF) without phase reversal for at least 95% of the object vergences within the range of −2.5 to 0 Diopter (D) when said optic is inserted into the model eye having an aperture size of 4 to 6 millimeters.

118. The lens pair of Example 117, wherein anterior and posterior surfaces of said second lens are shaped to provide modulation transfer functions (MTF) without phase reversal for at least 98% of the object vergences within the range of −2.5 to 0 Diopter (D) when said optic is inserted into the model eye having an aperture size of 4 to 6 millimeters.

119. The lens pair of Example 118, wherein anterior and posterior surfaces of said second lens are shaped to provide modulation transfer functions (MTF) without phase reversal for at least 99% of the object vergences within the range of −2.5 to 0 Diopter (D) when said optic is inserted into the model eye having an aperture size of 4 to 6 millimeters.

120. The lens pair of Example 119, wherein anterior and posterior surfaces of said second lens are shaped to provide modulation transfer functions (MTF) without phase reversal for 100% of the object vergences within the range of −2.5 to 0 Diopter (D) when said optic is inserted into the model eye having an aperture size of 4 to 6 millimeters.

121. A lens configured for implantation into an eye of a human, said lens comprising:
an optic comprising transparent material, said optic having an anterior surface and a posterior surface, each of said anterior surface and said posterior surface having a surface vertex, said optic having an optical axis through said surface vertices, wherein at least one of said anterior and posterior surfaces comprises a surface having a first portion and a second portion, said first portion disposed centrally about the optical axis, said second portion surrounding said first portion and having a different surface profile than said first portion, said first portion configured to provide an extended depth of field, and said second portion configured to provide an enhanced vision quality metric at distance in comparison to said first portion.

122. The lens of Example 121, further comprising a third portion surrounding said second portion, said third portion having a different surface profile than said second portion.

123. The lens of Example 122, wherein said third portion has a similar surface profile as said first portion.

124. The lens of any of Examples 121-123, wherein said second portion is configured to provide an enhanced vision quality metric at distance in comparison to said third portion.

125. The lens of any of Examples 121-124, wherein the enhanced vision quality metric is a modulation transfer function, a contrast sensitivity, a derivation thereof, or a combination thereof.

126. The lens of any of Examples 121-125, wherein said first portion has a shape that comprises a conic, biconic, or biaspheric envelope offset by perturbations of the envelope comprising an aspheric higher order function of radial distance from the optical axis.

127. A lens configured for implantation into an eye of a human, said lens comprising:
an optic comprising transparent material, said optic having an anterior surface and a posterior surface, each of said anterior surface and said posterior surface having a surface vertex, said optic having an optical axis through said surface vertices,
wherein at least one of said anterior and posterior surfaces comprises a surface having a first portion and a second portion, said first portion having a shape that comprises a conic, biconic, or biaspheric envelope offset by perturbations with respect to the envelope comprising an aspheric higher order function of radial distance from the optical axis, and said second portion having a shape that comprises a conic, biconic, or biaspheric envelope not offset by perturbations of the envelope comprising an aspheric higher order function of radial distance from the optical axis.

128. The lens of Example 127, wherein said first portion is disposed centrally about the optical axis, and said second portion surrounds said first portion.

129. The lens of Example 127 or 128, further comprising a third portion surrounding said second portion, said third portion having a shape that comprises a conic, biconic, or biaspheric envelope offset by perturbations with respect to the envelope comprising an aspheric higher order function of radial distance from the optical axis.

130. The lens of Example 129, wherein said third portion has substantially the same conic, biconic, or biaspheric envelope offset by perturbations with respect to the envelope comprising an aspheric higher order function of radial distance from the optical axis as said first portion.

131. A lens configured for implantation into an eye of a human, said lens comprising:
an optic comprising transparent material, said optic having an anterior surface and a posterior surface, each of said anterior surface and said posterior surface having a surface vertex, said optic having an optical axis through said surface vertices,
wherein at least one of said anterior and posterior surfaces comprises a surface having a first portion and a second portion, said first portion disposed centrally about the optical axis, said second portion surrounding said first portion, said first portion having higher spherical aberration control that provides extended depth of field than said second portion.

132. The lens of Example 131, further comprising a third portion surrounding said second portion, said third portion having higher spherical aberration control that provides extended depth of field than said second portion.

133. The lens of Example 132, wherein said third portion has substantially the same spherical aberration control as said first portion.

134. The lens of any of Examples 131-133, wherein said first portion has a shape that comprises a conic, biconic, or biaspheric envelope offset by perturbations from the envelope comprising an aspheric higher order function of radial distance from the optical axis.

135. The lens of any of Examples 122-126 or any of Examples 132-134, wherein said third portion has a shape that comprises a conic, biconic, or biaspheric envelope offset by perturbations from the envelope comprising an aspheric higher order function of radial distance from the optical axis.

136. The lens of any of Examples 126-130 or any of Examples 134-135, wherein said aspheric higher order function includes a second order term, $a_2 r^2$, where $a_2$ is a coefficient and r is the radial distance from the optical axis.

137. The lens of any of Examples 126-130 or any of Examples 134-136, wherein said aspheric higher order function includes a fourth order term, $a_4 r^4$, where $a_4$ is a coefficient and r is the radial distance from the optical axis.

138. The lens of any of Examples 126-130 or any of Examples 134-137, wherein said aspheric higher order function includes a sixth order term, $a_6 r^6$ where $a_6$ is a coefficient and r is the radial distance from the optical axis.

139. The lens of any of Examples 126-130 or any of Examples 134-138, wherein said aspheric higher order function includes an eighth order term, $a_8 r^8$ where $a_8$ is a coefficient and r is the radial distance from the optical axis.

140. The lens of any of Examples 126-130 or any of Examples 134-139, wherein said aspheric higher order function includes at least one even order term, $a_{2n} r^{2n}$, where n is an integer and $a_{2n}$ is a coefficient and r is the radial distance from the optical axis.

141. The lens of any of Examples 121-140, further comprising a transition portion providing a smooth transition without discontinuity between said first and second portions.

142. The lens of Example 141, wherein said transition portion has a distance between inner and outer radii in the range of about 0.1-1 mm.

143. The lens of any of Examples 121-142, wherein said first portion has a maximum cross-sectional diameter in the range of about 2.5-4.5 mm.

144. The lens of Example 143, wherein said first portion has a maximum cross-sectional diameter of about 3.75 mm.

145. The lens of any of Examples 121-144, wherein said second portion has a distance between inner and outer radii in the range of about 1-3.5 mm.

146. The lens of any of Examples 122-126, any of Examples 129-130, or any of Examples 132-133, wherein said second portion has a distance between inner and outer radii in the range of about 0.25-1.5 mm.

147. The lens of any of Examples 121-146, wherein said optic has a thickness along said optical axis that is in the range of about 100-700 microns.

148. The lens of any of Examples 121-147, further comprising at least one haptic disposed with respect to the optic to affix the optic in the eye when implanted therein.

149. The lens of any of Examples 121-148, wherein said anterior surface comprises said surface having said first and second portions.

150. The lens of any of Examples 121-149, wherein said posterior surface comprises a shape having a biconic envelope.

151. A lens configured for implantation into an eye of a human, said lens comprising:
an optic comprising transparent material, said optic having an anterior surface and a posterior surface, each of said anterior surface and said posterior surface having a surface vertex, said optic having an optical axis through said surface vertices,
wherein at least one of said anterior and posterior surfaces comprises a surface having a first portion and a second portion, said first portion disposed centrally about the optical axis, said second portion surrounding said first portion, said first portion configured to provide an extended depth of field, and said second portion configured to provide a monofocal distance focusing.

152. The lens of Example 151, further comprising a third portion surrounding said second portion, said third portion configured to provide an extended depth of field.

153. The lens of Example 151 or 152, wherein said first portion has a shape that comprises a conic, biconic, or biaspheric envelope offset by perturbations with respect to the envelope comprising an aspheric higher order function of radial distance from the optical axis.

154. The lens of any of Examples 151-153, wherein said third portion has a shape that comprises a conic, biconic, or biaspheric envelope offset by perturbations with respect to the envelope comprising an aspheric higher order function of radial distance from the optical axis.

155. The lens of any of Examples 121-125, wherein distance comprise objects between infinity to 2 meters.

156. The lens of any of Examples 121-125, wherein distance comprises 0 D vergence.

157. The lens of any of Examples 121-156, wherein each of the first and second portions has a caustic, and wherein the second portion has a conic constant such that the caustic of the second portion blends smoothly with the caustic of the first portion.

158. The lens of any of Examples 122-123, any of Examples 129-130, any of Examples 132-133, or Example 152, wherein each of the second and third portions has a caustic, and wherein the second portion has a conic constant such that the caustic of the second portion blends smoothly with the caustic of the third portion.

159. The lens of any of Examples 121-156, wherein each of the first and second portions has a caustic, and wherein the second portion has a conic constant such that the caustic of the second portion blends more smoothly with the caustic of the first portion than if the second portion comprises a spherical surface.

160. The lens of any of Examples 122-123, any of Examples 129-130, any of Examples 132-133, or Example 152, wherein each of the second and third portions has a caustic, and wherein the second portion has a conic constant such that the caustic of the second portion blends more smoothly with the caustic of the third portion than if the second portion comprises a spherical surface.

161. The lens of any of Examples 121-146, wherein said optic has a thickness along said optical axis that is in the range of about 700 microns-4 millimeters.

162. The lens of any of Examples 121-161, wherein said anterior surface is convex.

163. The lens of any of Examples 121-161, wherein said posterior surface is concave.

164. The lens of any of Examples 121-163, wherein said anterior surface is convex and said posterior surface is concave such that said optic is meniscus shaped.

165. The lens of any of Examples 121-162, wherein said posterior surface is convex.

166. The lens of any of Examples 121-161 or Example 163, wherein said anterior surface is concave.

167. The lens of any of Examples 121-126, any of Examples 131-135, or any of Examples 151-156, wherein said second portion has a shape that comprises a conic, biconic, or biaspheric envelope not offset by perturbations of the envelope comprising an aspheric higher order function of radial distance from the optical axis.

168. The lens of Example 39, any of Examples 52-54, or Example 58, wherein said anterior surface is rotationally symmetric.

169. The lens of Example 39, any of Examples 52-54, or Example 58, wherein said anterior surface has a shape that includes a conic or biconic term.

170. The lens of Example 169, wherein said anterior surface has a shape that includes a conic or biconic term and aspheric higher order perturbation terms.

171. The lens of Example 168, wherein said posterior surface has a shape that includes a conic or biconic term.

172. The lens of Example 171, wherein said conic or biconic term has a conic constant having a magnitude greater than zero.

173. The lens of Example 172, wherein said conic or biconic term has a conic constant having a magnitude of at least one.

174. The lens of Example 173, wherein said conic or biconic term has a conic constant having a magnitude of at least ten.

175. The lens of any of Examples 168-170, wherein said posterior surface is rotationally non-symmetric and has different curvature along different directions through said optical axis of said optic.

176. The lens of Example 175, wherein said posterior surface has different curvature along orthogonal directions through said optical axis of said optic.

177. The lens of any of Examples 168-169, wherein said posterior surface is rotationally non-symmetric and has a shape that includes a biconic term.

178. The lens of Example 177, wherein said biconic term has a conic constant having a magnitude greater than zero.

179. The lens of Example 178, wherein said biconic term has a conic constant having a magnitude of at least one.

180. The lens of Example 179, wherein said biconic term has a conic constant having a magnitude of at least ten.

181. The lens of any of Examples 1-47 or any of Examples 52-96, wherein at least one of said anterior and posterior surfaces comprises a surface having a first portion and a second portion, said first portion disposed centrally about the optical axis, said second portion surrounding said first portion and having a different surface profile than said first portion, said first portion configured to provide an extended depth of field, and said second portion configured to provide an enhanced vision quality metric at distance in comparison to said first portion.

182. The lens of Example 181, further comprising a third portion surrounding said second portion, said third portion having a different surface profile than said second portion.

183. The lens of Example 182, wherein said third portion has a similar surface profile as said first portion.

184. The lens of any of Examples 181-183, wherein said second portion is configured to provide an enhanced vision quality metric at distance in comparison to said third portion.

185. The lens of any of Examples 181-184, wherein the enhanced vision quality metric is a modulation transfer function, a contrast sensitivity, a derivation thereof, or a combination thereof.

186. The lens of any of Examples 181-185, wherein said first portion has a shape that comprises a conic, biconic, or biaspheric envelope offset by perturbations of the envelope comprising an aspheric higher order function of radial distance from the optical axis.

187. The lens of any of Examples 181-186, wherein said second portion has a shape that comprises a conic, biconic, or biaspheric envelope not offset by perturbations of the envelope comprising an aspheric higher order function of radial distance from the optical axis.

188. The lens of any of Examples 182-183, wherein said third portion has a shape that comprises a conic, biconic, or biaspheric envelope offset by perturbations of the envelope comprising an aspheric higher order function of radial distance from the optical axis.

189. A method of manufacturing a lens configured for implantation into an eye of a human, the method comprising:
    forming the lens of any of Examples 1-47, any of Examples 52-87, any of Examples 90-96, or any of Examples 121-188.

190. A method of manufacturing a lens pair configured for implantation into a pair of left and right eyes of a human, the method comprising:
    forming the lens pair of any of Examples 48-51 or any of Examples 97-120.

191. A lens configured for implantation into an eye of a human, said lens comprising:
    an optic comprising transparent material, said optic having an anterior surface and a posterior surface, each of said anterior surface and said posterior surface having a surface vertex, said optic having an optical axis through said surface vertices,
    at least one haptic disposed with respect to the optic to affix the optic in the eye when implanted therein,
    wherein said anterior and posterior surfaces comprise aspheric surfaces and said posterior surface has an aspheric shape that comprises a biconic offset by perturbations comprising an aspheric higher order function of radial distance from the optical axis,
    wherein the posterior surface has an absolute value of ratio $R_x/R_y$ between 0 and 100 and an absolute value of ratio $k_x/k_y$ between 0 and 100.

192. The lens of Example 191, wherein the absolute value of the ratio $R_x/R_y$ is between 0 and 75.

193. The lens of Example 192, wherein the absolute value of the ratio $R_x/R_y$ is between 0 and 50.

194. The lens of Example 193, wherein the absolute value of the ratio $R_x/R_y$ is between 0 and 25.

195. The lens of Example 194, wherein the absolute value of the ratio $R_x/R_y$ is between 0 and 10.

196. The lens of any of Examples 191-195, wherein the absolute value of the ratio $k_x/k_y$ is between 0 and 75.

197. The lens of Example 196, wherein the absolute value of the ratio $k_x/k_y$ is between 0 and 50.

198. The lens of Example 197, wherein the absolute value of the ratio $k_x/k_y$ is between 0 and 25.

199. The lens of Example 198, wherein the absolute value of the ratio $k_x/k_y$ is between 0 and 10.

200. A lens configured for implantation into an eye of a human, said lens comprising:

an optic comprising transparent material, said optic having an anterior surface and a posterior surface, said anterior surface or posterior surface comprising an aspheric surface,
wherein the anterior and posterior surfaces are shaped to provide a Salvador Image Quality (SIQ) metric that is at least 0.6 for at least 90% of the object vergences within the range of 0 to +1.5 Diopter (D) when said optic is inserted into said human eye having an aperture size of 4 to 6 millimeters.

201. The lens of Example 200, wherein the anterior and posterior surfaces are shaped to provide the SIQ that is at least 0.6 for at least 95% of the object vergences within the range of 0 to +1.5 Diopter (D).

202. The lens of Example 201, wherein the anterior and posterior surfaces are shaped to provide the SIQ that is at least 0.6 for at least 98% of the object vergences within the range of 0 to +1.5 Diopter (D).

203. The lens of Example 202, wherein the anterior and posterior surfaces are shaped to provide the SIQ that is at least 0.6 for at least 98% of the object vergences within the range of 0 to +2.5 Diopter (D).

204. A lens configured for implantation into an eye of a human, said lens comprising:
an optic comprising transparent material, said optic having an anterior surface and a posterior surface, said anterior surface or posterior surface comprising an aspheric surface,
wherein the anterior and posterior surfaces are shaped to provide an above average psychophysical grade for at least 90% of the object vergences within the range of 0 to +1.5 Diopter (D) when said optic is inserted into said human eye having an aperture size of 4 to 6 millimeters or into a model eye having an aperture size of 4 to 6 millimeters.

205. The lens of Example 204, wherein the anterior and posterior surfaces are shaped to provide the above average psychophysical grade for at least 95% of the object vergences within the range of 0 to +1.5 Diopter (D).

206. The lens of Example 205, wherein the anterior and posterior surfaces are shaped to provide the above average psychophysical grade for at least 98% of the object vergences within the range of 0 to +1.5 Diopter (D).

207. The lens of Example 206, wherein the anterior and posterior surfaces are shaped to provide the above average psychophysical grade for at least 98% of the object vergences within the range of 0 to +2.5 Diopter (D).

208. The lens of any of Examples 200-207, wherein the aperture size is 6 millimeters.

209. The lens of any of Examples 200-208, wherein each of said anterior surface and said posterior surface has a surface vertex, said optic having an optical axis through said surface vertices, and
wherein said anterior or posterior surface has an aspheric shape that comprises a biconic offset by perturbations comprising an aspheric higher order function of radial distance from the optical axis.

210. The lens of any of Examples 191-199 or Example 209, wherein said optic comprises an exit pupil, and
wherein the anterior and posterior surfaces are shaped to provide a radial power profile characterized by $\Phi(r) = a + br^2 + cr^4 + dr^6 + er^8$ for wavefront at the exit pupil of the optic for an object vergence of 0 to 2.5 Diopter (D) where r is the radial distance from the optical axis and a, b, c, d, and e are coefficients.

211. The lens of any of Examples 191-199 or any of Examples 209-210, wherein a thickness along said optical axis is between about 100-700 micrometers.

212. The lens of any of the preceding Examples, wherein said anterior surface is convex and said posterior surface is concave such that said optic is meniscus shaped.

213. The lens of Example 191, wherein the absolute value of the ratio $R_x/R_y$ is between 0.1 and 10.

214. The lens of Example 213, wherein the absolute value of the ratio $R_x/R_y$ is between 0.2 and 10.

215. The lens of Example 214, wherein the absolute value of the ratio $R_x/R_y$ is between 0.25 and 10.

216. The lens of Example 215, wherein the absolute value of the ratio $R_x/R_y$ is between 0.5 and 10.

217. The lens of any of Examples 191-195 or any of Examples 213-216, wherein the absolute value of the ratio $k_x/k_y$ is between 0.1 and 10.

218. The lens of Example 217, wherein the absolute value of the ratio $k_x/k_y$ is between 0.2 and 10.

219. The lens of Example 218, wherein the absolute value of the ratio $k_x/k_y$ is between 0.25 and 10.

220. The lens of Example 219, wherein the absolute value of the ratio $k_x/k_y$ is between 0.5 and 10.

BRIEF DESCRIPTION OF THE DRAWINGS

FIG. 3B is the cross sectional side view of the example lens shown in FIG. 2.

FIG. 4 is a schematic of the cross sectional side view of the optic of the lens shown in FIG. 2.

FIG. 5A is a schematic of an example positive meniscus optic.

FIG. 5B is a schematic of an example negative meniscus optic.

DETAILED DESCRIPTION

Figure 1:
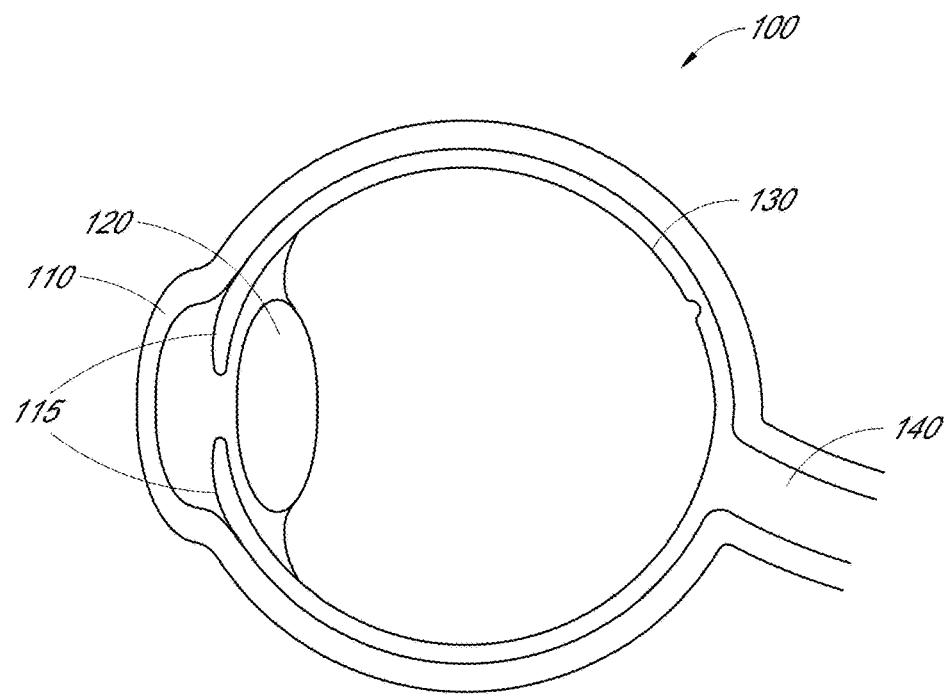
FIG. 1 is a schematic illustration of the human eye.

Vision problems, such as myopia (nearsightedness), hyperopia (farsightedness), and astigmatism, have been corrected using eyeglasses and contact lenses. Surgical techniques, e.g., laser assisted in-situ keratomileusis (LASIK), have become more common to help address the inconvenience of eyeglasses and contact lenses. In LASIK, a laser is used to cut a flap in the cornea to access the underlying tissue, and to alter the shape of the cornea. In addition, an intraocular lens (IOL) has been used to help treat myopia and cataracts (clouding of the natural crystalline lens of the eye) by replacing the natural lens of with a pseudophakic lens configured to be secured within the capsular bag.

Another solution to treat imperfections in visual acuity is with phakic IOLs. Phakic IOLs are transparent lenses implanted within the eye without the removal of the natural crystalline lens. Accordingly, the phakic IOL together with the cornea and the crystalline lens provide optical power for imaging an object onto the retina. (In contrast, pseudophakic IOLs, which are lenses implanted within the eye to replace the natural lens, e.g., after removal of the cloudy natural lens to treat cataracts as described above.) Implantation of a phakic IOL can be employed to correct for myopia, hyperopia, as well as astigmatism, freeing a patient from the inconvenience of eyewear and contacts. Phakic IOL can also be removed, bringing the optics of the eye back toward a natural condition, or replaced to address changing vision correction or enhancement needs of the eye.

With age, people develop presbyopia (inability to focus on near objects), which has been addressed with reading glasses in order to provide the extra refractive power lost when accommodation for near objects is no longer attainable. Multifocal contact lenses and IOLs, which provide discrete foci for near and far vision, have also been used, but the losses in contrast sensitivity and the presence of coaxial ghost images in the patient's field of view have made the acceptance of such solutions limited.

Certain embodiments described herein can advantageously provide ophthalmic implants for vision correction of, including but not limited to, myopia, hyperopia, astigmatism, cataracts, and/or presbyopia with extended depth of field and enhanced visual acuity. In various embodiments, the ophthalmic implants include a lens configured for implantation into an eye of a patient, for example, a human being. Such lenses are particularly useful for treating presbyopia and onset of presbyopia in middle age populations.

Certain embodiments can include phakic lens implants, where the lens can be implanted in front of the natural crystalline lens 120, such as between the cornea 110 and the iris 115. Other embodiments are configured to be placed between the iris 115 and natural crystalline lens 120. Some example embodiments include lenses for treating myopia, hyperopia, astigmatism, and/or presbyopia.

Some other embodiments can include a pseudophakic lens implanted within the eye, for example, in the capsular bag, after removal of the crystalline lens 120. As discussed above, a pseudophakic lens can be used for treating cataracts as well as for providing refractive correction.

Figure 2:
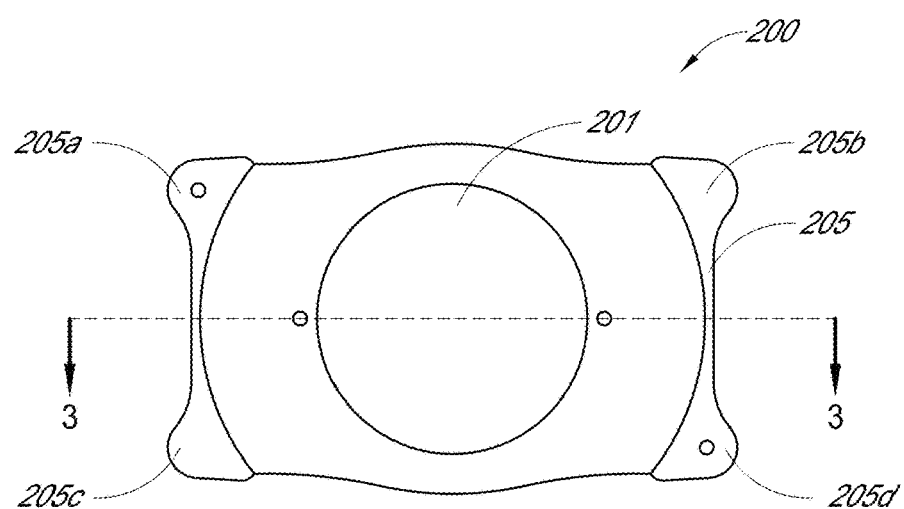
FIG. 2 is an example lens according to certain embodiments described herein.

FIG. 2 is an example lens 200 according to various embodiments described herein. The lens 200 can include an optical zone or optic 201. The optic 201 transmits and focuses, e.g., refracts, light received by the lens 200. As will be described in more detail herein, the optic 201 can comprise a surface shape of one or more surfaces of the optic 201 designed to refract and focus light and increase the depth of field and visual acuity. For example, in some embodiments, the surface shapes of the surfaces of the optic 201 can be designed such that the optic 201 can continuously focus light for high visual acuity, e.g., 20/20 vision, for a wide range of object vergences (e.g., vergences within the range of at least about 0 to about 2.5 Diopter, in some implementations from at least about 0 diopter to at least about 1.8, 1.9, 2.0, 2.1, 2.2, 2.3, 2.4, 2.5, 2.6, 2.7, 2.8, 2.9, or 3.0 diopters or possibly from at least about 0.1, 0.2, 0.3, 0.4, 0.5, 0.6, or 0.7 diopter to at least about 2.5, 2.6, 2.7, 2.8, 2.9, or 3.0 diopters) onto the retina to increase the depth of field. Furthermore, in some embodiments, the surface shapes of the surfaces of the optic 201 can be designed such that the images are substantially coaxial and of substantially similar magnitude to reduce the presence of ghost images.

As shown in FIG. 2, the example lens 200 can also include a haptic 205. In some embodiments, the haptic 205 can include one or more haptics or haptic portions 205a, 205b, 205c, and 205d to stabilize the lens in and attach the lens 200 to the eye. For example, in FIG. 2, the haptic portions 205a, 205b, 205c, and 205d are disposed about the optic 201 to affix the optic 201 in the eye when implanted therein. In certain embodiments the haptic portions 205a, 205b, 205c, and 205d are configured to stabilize the optic 201 in the eye such that the optical axis of the optic 201 is disposed along a central optical axis of the eye. In such embodiments, the stability of the wavefront of the optic 201 in the eye can be provided by the haptic portions 205a, 205b, 205c, and 205d. In various embodiments, the lens and in particular the haptics are configured to be implanted outside the capsulary bag, for example, forward the natural lens as for a phakic IOL design. As discussed above, the phakic IOL implant may be configured for implantation between the iris and the natural lens. Accordingly, in certain embodiments, the haptic 205 is vaulted such that the optic 201 is disposed along a central optical axis of the eye at a location anterior of the location of contact points between the haptic portions 205a-205d. The configuration enhances clearance between the optic 201 and the natural lens in a phakic eye, which natural lens flexes when the eye accommodates. In some cases, the haptic 205 is configured to provide minimum clearance to the natural lens when implanted that reduce, minimize or prevents contact between an anterior surface of the natural lens and a posterior surface of the optic 201. With some materials, contact between the optic 201 and the anterior surface of the natural lens is permitted. In some embodiments, the lens 200 can be implanted across the pupil or the opening of the iris 115, and when in place, the haptic portions 205a, 205b, 205c, and 205d can be placed under the iris 115. Although the haptic 205 shown in FIG. 2 includes four haptic portions 205a, 205b, 205c, and 205d in the shape of extended corner portions, the shape, size, and number of haptics or haptic portions are not particularly limited.

Figure 3A:
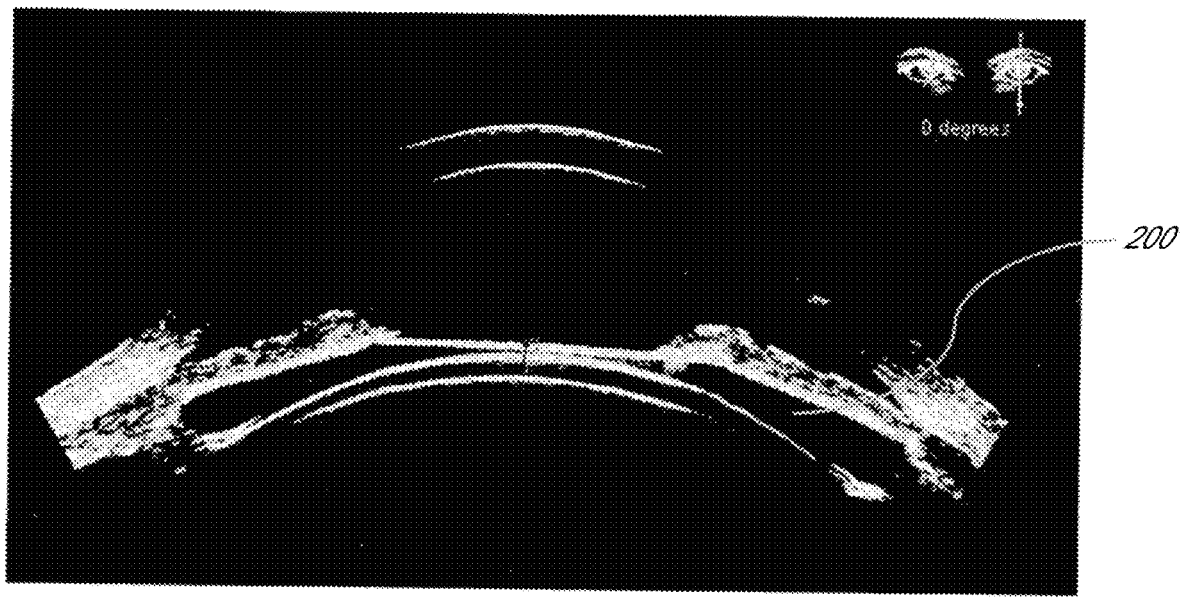
FIG. 3A is an ultrasound of an example lens 200 in accordance with certain embodiments described herein implanted in the eye.

In various implementations, for example, the lens is configured for implantation within the capsular bag after removal of the natural lens. Such pseudophakic lens may have haptics having a shape, size and/or number suitable for providing secure placement and orientation within the capsular bag after implantation. FIG. 3A is an ultrasound of an example lens 200 in accordance with certain embodiments described herein implanted in the eye.

The optic 201 can include a transparent material. For example, the transparent material can include a collagen copolymer material, a hydrogel, a silicone, and/or an acrylic. In some embodiments, the transparent material can include a hydrophobic material. In other embodiments, the transparent material can include a hydrophilic material. Other materials known or yet to be developed can be used for the optic 201.

Certain embodiments of the optic 201 can advantageously include a collagen copolymer material, e.g., similar to material used in Collamer® IOLs by STAAR® Surgical Company in Monrovia, Calif. An example collagen copolymer material is hydroxyethyl methacrylate (HEMA)/porcine-collagen based biocompatible polymer material. Since collagen copolymer materials can have characteristics similar to that of the human crystalline lens, certain embodiments of the lens described herein can perform optically similar to the natural lens. For example, in some embodiments, due to the anti-reflective properties and water content of about 40%, a lens 200 made with a collagen copolymer material can transmit light similar to the natural human crystalline lens. Less light can be reflected within the eye, leading to sharper, clearer vision, and fewer occurrences of glare, halos, or poor night vision compared with lenses made with other lens materials.

In some embodiments of the lens 200 made with a collagen copolymer material, the lens 200 can be flexible, allowing easy implantation within the eye. In addition, because collagen copolymer materials are made with collagen, various embodiments of the lens 200 are biocompatible with the eye. In some embodiments, the lens 200 can attract fibronectin, a substance found naturally in the eye. A layer of fibronectin can form around the lens 200, inhibiting white cell adhesion to the lens 200. The coating of fibronectin can help prevent the lens 200 from being identified as a foreign object. In addition, like the collagen it contains, various embodiments of the lens 200 can carry a slight negative charge. Since proteins in the eye also carry a negative charge, as these two negative forces meet along the border of the lens 200, the charge repulsion can help push away the proteins from the lens 200. As such, the lens 200 can naturally keep itself clean and clear.

Furthermore, in some embodiments, the lens 200 can include an ultraviolet (UV) blocker. Such a blocker can help prevent harmful UVA and UVB rays from entering the eye. Accordingly, certain embodiments can help prevent the development of UV related eye disorders.

In some embodiments, the haptic 205 (or one or more of the haptic portions 205a, 205b, 205c, and 205d) can also be made of the same material as the optic 201. For example, the haptic 205 can be made of a collagen copolymer, a hydrogel, a silicone, and/or an acrylic. In some embodiments, the haptic 205 can include a hydrophobic material. In other embodiments, the haptic 205 can include a hydrophilic material. Other materials known or yet to be developed can also be used for the haptic 205.

The lens 200 can be manufactured by diamond turning, molding, or other techniques known in the art or yet to be developed. In some embodiments of the lens 200 manufactured with a collagen copolymer material, the lens 200 can be machined in a dry state, followed by hydration to stabilize the lens 200. A similar approach can be employed for other material as well.

FIG. 3B is the cross sectional side view of the example lens 200 shown in FIG. 2; and FIG. 4 is a schematic of the cross sectional side view of the optic 201 of the lens 200. The optic 201 has an anterior surface 201a and a posterior surface 201b. The optic 201 also has a center through which the optical axis of the lens passes and a thickness $T_c$ at the center along the optical axis. The optical axis passes through the surface vertices of the anterior and posterior surfaces 201a, 201b. The exact size of the optic 201 can depend on the patient's pupil size, the material of the lens 200, and the patient's prescription. In some embodiments, for example, for phakic lenses, the thickness at the center $T_c$ of the optic 201 can be made relatively thin. For example, the thickness at the center $T_c$ of the optic 201 can be about 100 to about 700 micrometers, about 100 to about 600 micrometers, about 100 to about 500 micrometers, about 100 to about 400 micrometers, about 100 to about 300 micrometers, or about 100 to about 200 micrometers, such that the lens 200 can be relatively unnoticeable to the patient and to others. Thinner lenses also simplify the process of insertion of the lens through the eye tissue, e.g., cornea. For example, the optic could have a thickness along the optical axis of about 110, 115, 120, 130, 140, or 150 to about 200, 300, or 400 micrometers, any values between any of these thicknesses, or any ranges formed by any of these thicknesses. The thickness at the center $T_c$ of the optic 201 can thus be any thickness in between the above mentioned values, e.g., thickness in ranges between any of the following: 100 micrometers, 110 micrometers, 115 micrometers, 120 micrometers, 130 micrometers, 140 micrometers, 150 micrometers, 200 micrometers, 250 micrometers, 300 micrometers, 350 micrometers, 400 micrometers, 450 micrometers, 500 micrometers, 550 micrometers, 600 micrometers, 650 micrometers, or 700 micrometers.

In some other embodiments for example, for pseudophakic lenses where the lens 201 replaces the natural crystalline lens, the thickness at the center $T_c$ of the optic 201 can be thicker than those for phakic lenses, e.g., about 700 micrometers to about 4 mm, about 700 micrometers to about 3 mm, about 700 micrometers to about 2 mm, about 700 micrometers to about 1 mm, any value in between such ranges, or any ranges formed by any of the values in these ranges. For example, the thickness at the center $T_c$ of the optic 201 can be about 700 micrometers, about 800 micrometers, about 900 micrometers, about 1 millimeter, about 1.5 millimeters, about 2 millimeters, about 2.5 millimeters, about 3 millimeters, about 3.5 millimeters, or about 4 millimeters or ranges therebetween. However, even for pseudophakic lenses the lens may employ smaller thicknesses, $T_c$, for example, thicknesses between about 300 micrometers to 700 micrometers, for example, 300 micrometers, 400 micrometers, 500 micrometers, 600 micrometers or 700 micrometers or any ranges therebetween such as 300 to 400 micrometer, 400 to 500 micrometers, 500 to 600 micrometers.

In accordance with certain embodiments described herein, the anterior surface 201a is convex and the posterior surface 201b is concave such that the optic 201 is meniscus shaped. FIGS. 5A and 5B are example cross sectional side views of the optic 201 being meniscus shaped. A meniscus shaped optic 201 can be quite advantageous when used for example, in a phakic lens. For example, when implanted behind (or posterior of) the iris and in front of (or anterior of) the natural lens, an anterior surface 201a of the optic 201 that is convex can help prevent chaffing of the iris adjacent to that surface 201a, and a posterior surface 201b of the optic 201a that is concave can help prevent damage to the natural lens adjacent to that surface 201b, which may result in, for example, cataracts.

The meniscus shaped optic can be described as either positive or negative. As shown in FIG. 5A, a positive meniscus optic 301 has a steeper curving convex surface 301a than the concave surface 301b, and has a greater thickness at the center $T_c$ (through which the optical axis passes) than at the edge $T_e$. In contrast, as shown in FIG. 5B, a negative meniscus optic 401 has a steeper curving concave surface 401b than the convex surface 401a, and has a greater thickness at the edge $T_e$ than at the center $T_c$. In certain embodiments, a positive meniscus optic can be used to treat hyperopia, while in other embodiments, a negative meniscus optic can be used to treat myopia.

In various embodiments, the optic 201 is not meniscus shaped. For example, in some embodiments, the anterior surface 201a is substantially flat and the posterior surface 201b is concave such that the optic 201 is plano-concave. In other embodiments, both the anterior surface 201a and the posterior surface 201b are concave such that the optic 201 is biconcave. In further embodiments, the anterior surface 201*a* is convex and the posterior surface 201*b* is substantially flat such that the optic 201 is plano-convex. In yet further embodiments, both the anterior surface 201*a* and the posterior surface 201*b* are convex such that the optic 201 is biconvex.

In certain embodiments, the anterior surface 201*a* and/or the posterior surface 201*b* of the optic 201 can include aspheric surfaces. For example, the anterior surface 201*a* and/or the posterior surface 201*b* of the optic 201 can include a surface shape that is not a portion of a sphere. In various embodiments, the anterior surface 201*a* and/or the posterior surface 201*b* can be rotationally symmetric. For example, the surface profile or sag of the aspheric shape can include at least a conic term. The conic term can be described as:

$$z = \frac{cr^2}{1 + \sqrt{1 - (1+k)c^2r^2}}, \quad (1)$$

where c is the curvature of the surface (or the inverse of the radius), k is the conic constant, and r is the radial distance from the surface vertex.

In some embodiments, the aspheric shape can include a conic offset by perturbations comprising, for example, a higher order function of radial distance from the surface vertex. Thus, the sag of the aspheric shape can include the conic term and a higher order function of radial distance from the surface vertex. The higher order function can describe the aspheric perturbations from the conic term. In some embodiments, the higher order function can include at least one even order term $a_{2n}r^{2n}$, where n is an integer, $a_{2n}$ is a coefficient, and r is the radial distance from the surface vertex. For example, the aspheric shape can be described using the conic term and the even-powered polynomial terms (e.g., describing an even asphere):

$$z(r) = \frac{cr^2}{1 + \sqrt{1 - (1+k)c^2r^2}} + a_2r^2 + a_4r^4 + a_6r^6 + a_8r^8 + \ldots \quad (2)$$

As can be seen in the example equation (2), the higher order function can include at least a second order term ($a_2r^2$), a fourth order term ($a_4r^4$), a sixth order term, ($a_6r^6$), and/or an eighth order term ($a_8r^8$). In some embodiments, the higher order function can include one or more odd order terms. For example, the higher order function can include only odd order terms or a combination of even and odd order terms.

As also shown in equation (2), the surface shape can depend on the conic constant k. If the conic constant k=0, then the surface is spherical. Thus, in some embodiments, k has a magnitude of at least zero, such that $|k| \geq 0$. In some embodiments, k has a magnitude greater than zero, such that $|k| \geq 0$. In various embodiments, k has a magnitude of at least one, such that $|k| \geq 1$. In some embodiments, $|k| \geq 2$, $|k| \geq 3$, $|k| \geq 5$, $|k| \geq 7$, or $|k| \geq 10$. For example, $k \leq -1$, $k \leq -2$, $k \leq -3$, $k \leq -5$, $k \leq -7$, $k \leq -10$. In various embodiments, therefore, the surface has a shape of a hyperbola. However, in certain embodiment, the magnitude of the conic constant may be less than one, e.g., $0 \leq |k| \leq 1$.

In various embodiments, the anterior surface 201*a* and/or the posterior surface 201*b* can be rotationally non-symmetric and have different curvature along different directions through the center and/or optical axis of the optic 201. For example, the anterior surface 201*a* and/or the posterior surface 201*b* can have different curvature along orthogonal directions through the center of the optic 201. Certain such embodiments can be advantageous for treating astigmatism, where correction along different directions (meridians) can be desired.

In some embodiments, the sag of the rotationally non-symmetric surface can include at least a biconic term. A biconic surface can be similar to a toroidal surface with the conic constant k and radius different in the x and y directions. The biconic term can be described as:

$$z = \frac{c_x x^2 + c_y y^2}{1 + \sqrt{1 - (1+k_x)c_x^2 x^2 - (1+k_y)c_y^2 y^2}}, \quad (3)$$

where $c_x$ is the curvature of the surface in the x direction (or the inverse of the radius in the x direction), and $c_y$ is the curvature of the surface in the y direction (or the inverse of the radius in the y direction) while $k_x$ is the conic constant for the x direction, and $k_y$ is the conic constant for the y direction.

In some embodiments, the aspheric shape can include the biconic offset by perturbations comprising a higher order function of radial distance from the surface vertex. Thus, similar to equation (2), the sag of the aspheric shape can include the biconic term and a higher order function. The higher order function can include at least one even order term, e.g., at least a second order term ($a_2r^2$), a fourth order term ($a_4r^4$), a sixth order term, ($a_6r^6$), and/or an eighth order term ($a_8r^8$). For example, similar to equation (2), the higher order function can be $a_2r^2 + a_4r^4 + a_6r^6 + a_8r^8 + \ldots$.

In some embodiments, the higher order function can include one or more odd order terms. For example, the higher order function can include only odd order terms or a combination of even and odd order terms.

Accordingly, as described herein, the anterior surface 201*a* and/or the posterior surface 201*b* of the optic 201 can have a shape that includes a conic term (with or without a higher order function) or a biconic term (with or without a higher order function).

One example for vision correction for presbyopia and/or astigmatism includes an anterior surface 201*a* and a posterior surface 201*b* both having an aspheric surface. The aspheric surface of the anterior surface 201*a* has a shape that includes a conic term offset by perturbations comprising second, fourth, sixth, and eighth order terms; and the aspheric surface of the posterior surface 201*b* has a shape that includes a biconic term. The sag of the example aspheric anterior surface 201*a* can be given as:

$$z(r) = \frac{cr^2}{1 + \sqrt{1 - (1+k)c^2r^2}} + a_2r^2 + a_4r^4 + a_6r^6 + a_8r^8. \quad (4)$$

Furthermore, the sag of the example posterior surface 201*b*, which can be biconic, can be given as:

$$z = \frac{c_x x^2 + c_y y^2}{1 + \sqrt{1 - (1+k_x)c_x^2 x^2 - (1+k_y)c_y^2 y^2}}, \quad (5)$$

which is similar to equation (3). Certain embodiments of such a lens may be, although is not limited to, a meniscus lens.

Other examples are possible. In certain embodiments, the particular shape (e.g., curvature of anterior surface, curvature of posterior surface, conic constants, coefficients of the higher order function, etc.) of the optic 201 can depend on the patient's prescription.

As some examples, for lenses having a nominal dioptric power between about −18 D to about 6 D sphere with 0 to about 2 D cylinder, with 0 to about 3 D cylinder, or with 0 to about 4 D cylinder, the following non-limiting example design parameters can be used in certain embodiments. The radius R of the anterior surface (e.g., the inverse of the curvature) can be between about −100 mm to about 100 mm, about −50 mm to about 50 mm, about −10 mm to about 10 mm, or about −5 mm to about 5 mm. In some examples, R of the anterior surface can be between about −1 mm to about 1 mm or 0 to about 1 mm. For example, the radius of the anterior surface can be between 0 to about $1 \times 10^{-2}$ mm, between about $1 \times 10^{-7}$ mm to about $5 \times 10^{-3}$ mm, between about $1 \times 10^{-6}$ mm to about $1 \times 10^{-3}$ mm, or between about $5 \times 10^{-6}$ mm to about $5 \times 10^{-4}$ mm.

As described herein, in various embodiments, k of the anterior surface can have a magnitude greater than zero such that $|k|>0$. In some embodiments, k has a magnitude of at least one, such that $|k| \geq 1$. In some embodiments, $|k| \geq 2$, $|k| \geq 3$, $|k| \geq 5$, $|k| \geq 7$, or $|k| \geq 10$. For example, $k \leq -1$, $k \leq -2$, $k \leq -3$, $k \leq -5$, $k \leq -7$, $k \leq -10$. In some embodiments, $k \ll -10$. For example, in some embodiments, k can be between about $-1 \times 10^6$ to $-100$, between about $-5 \times 10^5$ to about $-5 \times 10^4$, or between about $-3 \times 10^5$ to about $-2 \times 10^5$.

Accordingly, in various embodiments the magnitude of the ratio of the conic constant of the anterior surface and the radius of curvature of the anterior surface may be between $10^4$ and $10^{14}$, between $10^6$ and $10^{12}$, between $10^8$ and $10^{11}$, between $10^9$ and $10^{11}$, between $10^8$ and $10^{10}$, between $10^9$ and $10^{10}$, in various embodiments.

The coefficient $a_2$ for the second order term of the anterior surface in various embodiments can be between 0 to about 1. For example, $a_2$ can be between 0 to about 0.5, between about 0.001 to about 0.3, or between about 0.005 to about 0.2.

The coefficient $a_4$ for the fourth order term of the anterior surface in various embodiments can be between about −1 to 0. For example, $a_4$ can be between about −0.1 to 0, between about −0.05 to about $-1 \times 10^{-4}$, or between about −0.01 to about $-1 \times 10^{-3}$.

The coefficient $a_6$ for the sixth order term of the anterior surface in various embodiments can be between 0 to about 1. For example, $a_6$ can be between 0 to about 0.1, between 0 to about 0.01, or between about 0.0001 to about 0.001.

In addition, the coefficient $a_8$ for the eighth order term of the anterior surface in various embodiments can be between about −1 to 0. For example, $a_8$ can be between about −0.001 to 0, between about −0.0005 to 0, or between about −0.0001 to 0.

Furthermore, for lenses having a nominal dioptric power between about −18 D to about 6 D sphere with 0 to about 2 D cylinder, with 0 to about 3 D cylinder, or with 0 to about 4 D cylinder, the following non-limiting example design parameters can be used in certain embodiments for the posterior surface. The radius $R_y$ of the posterior surface in the y direction (e.g., the inverse of the curvature in the y direction) can be between 0 to about 20 mm. For example, the radius $R_y$ of the posterior surface can be between 0 to about 15 mm, between about 2 mm to about 13 mm, or between about 3 mm to about 14 mm, or between about 4 mm to about 10 mm.

In various embodiments, $k_y$ of the posterior surface can be between about −20 to about 20, between about −18 to about 15, or between about −15 to about 5. In some such embodiments, $k_y$ of the posterior surface does not necessarily have a magnitude of at least one. For example, $k_y$ can be between about −1 to about 1. In various embodiments, $|k_y|$ is greater than zero.

The radius $R_x$ of the posterior surface in the x direction (e.g., the inverse of the curvature in the x direction) can be between 0 to about 20 mm. For example, the radius of the posterior surface can be between 0 to about 15 mm, between 0 to about 12 mm, or between 0 to about 10 mm.

In various embodiments, $k_x$ of the posterior surface can be between about −25 to 0, between about −20 to 0, between about −18 to 0, between about −17.5 to 0, or between about −15.5 to 0. In various embodiments, $|k_x|$ is greater than zero.

In certain embodiments described herein, for lenses having a nominal dioptric power between about −18 D to about 6 D sphere with 0, 0.1, 0.2, 0.25, or 0.5 to about 10 D cylinder, or any ranges between any combination of these values (e.g., with 0.1 to about 2 D cylinder, with 0.5 to about 2 D cylinder, with 0.1 to about 3 D cylinder, with 0.5 to about 3 D cylinder, with 0.1 to about 4 D cylinder, with 0.5 to about 4 D cylinder, with 0.1 to about 5 D cylinder, with 0.5 to about 5 D cylinder, with 0.1 to about 6 D cylinder, with 0.5 to about 6 D cylinder, with 0.1 to about 7 D cylinder, with 0.5 to about 7 D cylinder, with 0.1 to about 8 D cylinder, with 0.5 to about 8 D cylinder, with 0.1 to about 9 D cylinder, with 0.5 to about 9 D cylinder, with 0.1 to about 10 D cylinder, with 0.5 to about 10 D cylinder, or any ranges between any combination of these values), the posterior surface can have a shape that includes a biconic term (with or without a higher order function). In some such embodiments, the posterior surface can have an absolute value of ratio $R_x/R_y$ between 0, 0.1, 0.2, 0.25, or 0.5 and 100, or any ranges between any combination of these values (e.g., between 0 and 100, between 0.1 and 100, between 0.5 and 100, between 0 and 75, between 0.1 and 75, between 0.5 and 75, between 0 and 50, between 0.1 and 50, between 0.5 and 50, between 0 and 25, between 0.1 and 25, between 0.5 and 25, between 0 and 10, between 0.1 and 10, or between 0.5 and 10, or any ranges between any combination of these values). In various embodiments, the absolute value of ratio $R_x/R_y$ is greater than zero. In addition, in some embodiments, the posterior surface can have an absolute value of ratio $k_x/k_y$ between 0, 0.1, 0.2, 0.25, or 0.5 and 100, or any ranges between any combination of these values (e.g., between 0 and 100, between 0.1 and 100, between 0.5 and 100, between 0 and 75, between 0.1 and 75, between 0.5 and 75, between 0 and 50, between 0.1 and 50, between 0.5 and 50, between 0 and 25, between 0.1 and 25, between 0.5 and 25, between 0 and 10, between 0.1 and 10, or between 0.5 and 10, or any ranges between any combination of these values). In various embodiments, the absolute value of ratio $k_x/k_y$ is greater than zero.

In some embodiments, the shape of the posterior surface can be related to the shape of the anterior surface. In some such embodiments, the posterior surface can have a shape that includes a biconic term (with or without a higher order function); and the anterior surface can have a shape that includes a conic term (with or without a higher order function). The relationship of the anterior and posterior surfaces can be non-linear. In various embodiments, a pattern can exist between $R_x$, $R_y$, $k_x$, $k_y$, of the posterior surface and the conic constant k of the anterior surface. For example, the absolute value of ratio $R_x/R_y$ can be as described herein, the absolute value of $k_x/k_y$ can be as described herein, and the conic constant k of the anterior surface can be less than $-2\times10^4$, and in some cases $\ll-2\times10^4$. For example, the conic constant k of the anterior surface can be between $-9\times10^5$ to $-1\times10^6$, between $-8\times10^5$ to $-1\times10^6$, between $-7\times10^5$ to $-1\times10^6$, between $-6\times10^5$ to $-1\times10^6$, or between $-5\times10^5$ to $-1\times10^6$.

In various embodiments described herein, the lenses may be utilized in a relatively low-to-zero spherical power configuration, with the addition of relatively significant cylindrical correction, e.g., greater than or equal to +1.0 D cylinder to the spherical base, in order to provide a given patient with better retinal image quality in cases where age-induced aberrations of the eye or cataract surgery-induced astigmatism may be negatively impacting the quality of life of the patient. For example, the low-to-zero spherical power configuration can include between 0, 0.1, 0.2, 0.25, or 0.5 to 3 D sphere, 1 to 3 D sphere, 2 to 5 D sphere, or 3 to 6 D sphere, with the addition of +1.0 D to +10 D cylinder or any ranges between these values (e.g, +1.0 D cylinder to +2.0 D cylinder, +2.0 D cylinder to +3.0 D cylinder, +3.0 D cylinder to +4.0 D cylinder, +4.0 D cylinder to +5.0 D cylinder, +5.0 D cylinder to +6 D cylinder, +6.0 D cylinder to +7.0 D cylinder, +7.0 D cylinder to +8.0 D cylinder, +8.0 D cylinder to +9.0 D cylinder, or +9.0 D cylinder to +10.0 D cylinder, or any ranges between any combination of these values) to the spherical base. In some embodiments, the ratio sphere/cylinder can be between 0, 0.1, 0.2, 0.25, or 0.5 to 6, or any ranges between any combination of these values (e.g., between 0 to 1, between 0.25 to 1, between 0 to 2, between 0.25 to 2, between 0 to 3, between 0.25 to 3, between 0 to 4, between 0.25 to 4, between 0 to 5, between 0.25 to 5, between 0 to 6, between 0.25 to 6, between 1 to 6, or between 2 to 6, or any ranges between any combination of these values).

Although the example design parameters of R, k, $a_2$, $a_4$, $a_6$, and $a_8$ for lenses having the above given nominal dioptric power were given for the anterior surface, and the example design parameters of $R_y$, $k_y$, $R_x$, $k_y$, ratio $R_x/R_y$, and ratio $k_x/k_y$ were given for the posterior surface, the ranges of values for R, k, $a_2$, $a_4$, $a_6$, and $a_8$ can be used for the posterior surface, and the ranges of values for $R_y$, $k_y$, $R_x$, and $k_x$, ratio $R_x/R_y$, and ratio $k_x/k_y$ can be used for the anterior surface. Additionally, although the anterior surface included the higher order aspheric perturbation terms (e.g., $a_2$, $a_4$, $a_6$, and $a_8$), the higher order aspheric perturbation terms (e.g., $a_2$, $a_4$, $a_6$, and $a_8$) can be used for the posterior surface instead of the anterior surface or for both the anterior and posterior surfaces. Any one or more of the values in these ranges can be used in any of these designs.

Figure 6A:
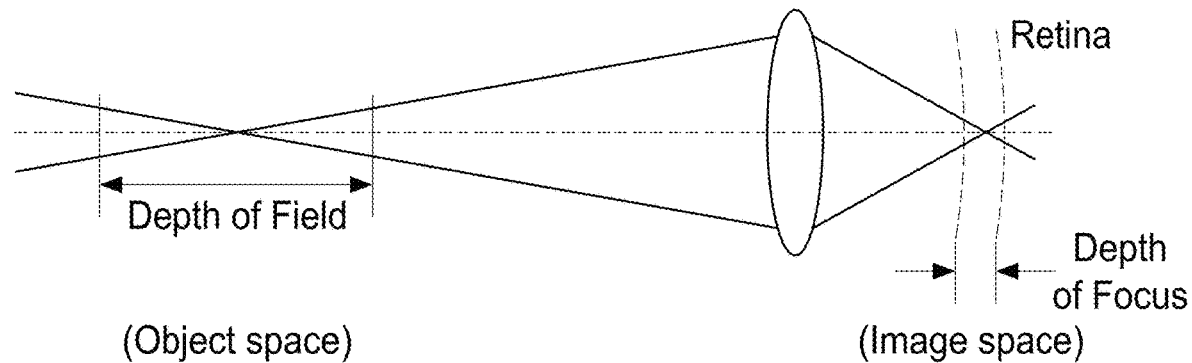
FIG. 6A schematically illustrates the depth of field in object space and the depth of focus in image space.

Furthermore, as described herein, the particular shape of various embodiments can be designed to increase the depth of field and to increase visual acuity. As shown in FIG. 6A, the depth of field can be described as the distance in front of and beyond the subject in object space that appears to be in focus. The depth of focus can be described as a measurement of how much distance exists behind the lens in image space wherein the image will remain in focus. To increase the depth of field, the surface shape of the anterior surface 201a and/or the surface shape of the posterior surface 201b of the optic 201 can be such that for a wide range of object vergences, the light rays are focused onto the retina or sufficiently close thereto. To increase visual acuity and reduce ghosting, the surface shape of the anterior 201a and/or the surface shape of the posterior surface 201b of the optic 201 also can be such that the images for an on-axis object are substantially on-axis and of similar magnitude with each other.

Figure 6B:
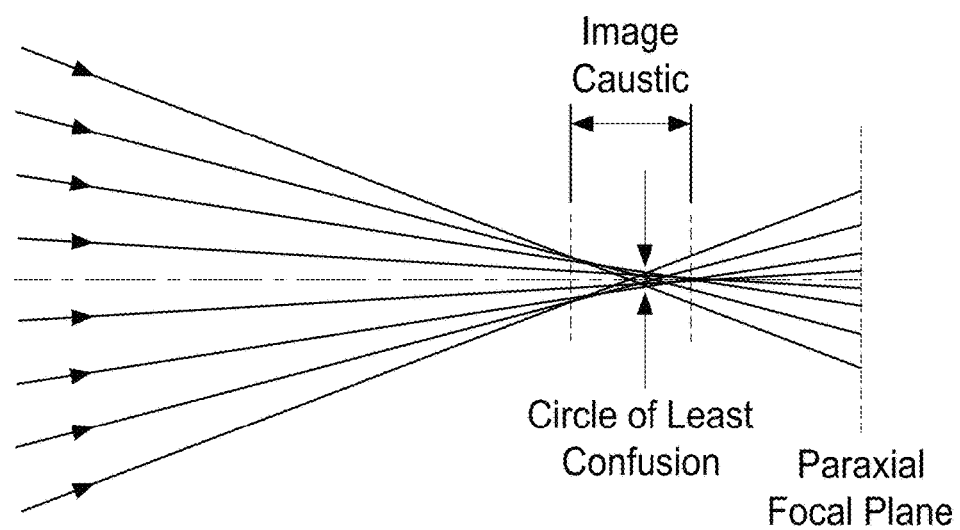
FIG. 6B schematically illustrates image caustic and circle of confusion.

In certain such embodiments, the image caustic can be sculpted for the vergence range of about 0 to about 2.5 Diopters or more although this range may be larger or smaller. As shown in FIG. 6B, in some embodiments, the image caustic can be described as the envelop produced by a grid of light rays, and the circle of confusion can be described as an optical spot caused by a cone of light rays from a lens not coming to a perfect focus when imaging a point source. Thus, the image caustic can be sculpted such that the circle of confusion is substantially stable having a similar sizes for a range of longitudinal positions along the optical axis and relatively small. The design may sacrifice the size of the circle of confusion at some longitudinal positions along the optical axis to permit the circle of confusion to be larger for others longitudinal positions with the net result of providing circles of confusion having similar size over a range of longitudinal positions along the optical axis.

In certain embodiments, the surface shape of the anterior surface 201a and/or the surface shape of the posterior surface 201b can be determined such that the image caustic is sculpted around the hyperfocal plane of the eye. In some embodiments, the hyperfocal distance can be described as the focus distance which places the maximum allowable circle of confusion at infinity, or the focusing distance that produces the greatest depth of field. Accordingly, in certain embodiments, to increase the depth of field, the surface shape of the anterior surface 201a and/or the surface shape of the posterior surface 201b of the optic 200 can be such that the light rays are refocused to the hyperfocal distance.

Figure 6C:
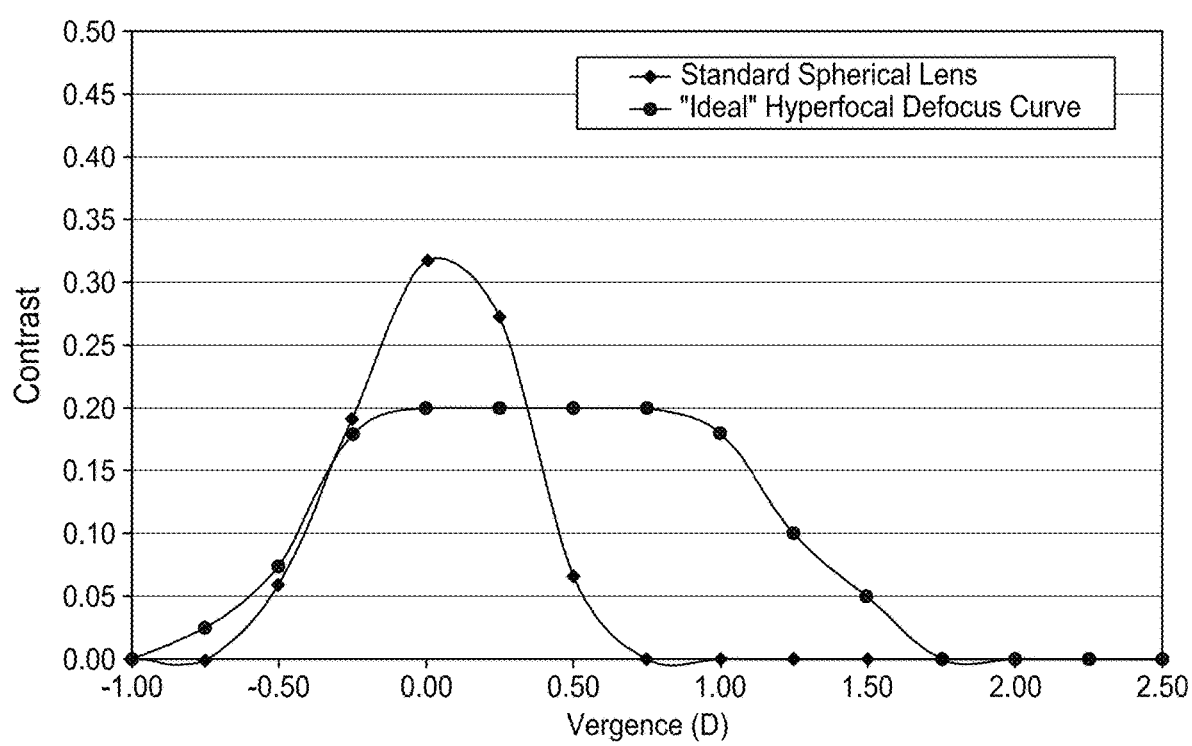
FIG. 6C schematically illustrates the defocus curves for a standard spherical lens and an idealized hyperfocal eye.

In various embodiments, the surface shape of the anterior surface 201a and/or the surface shape of the posterior surface 201b of the optic 201 can be evaluated and designed using the defocus curves of the lens. A defocus curve can portray the response of a retinal image quality parameter, such as contrast, as a function of different vergences. An object at infinity has a vergence of 0 Diopter. FIG. 6C illustrates the defocus curves for a standard spherical lens and an idealized hyperfocal eye. As shown in the figure, although the contrast can decrease (due to preservation of the areas under the curves), the idealized hyperfocal eye has a stable or substantially stable (e.g., similar or substantially constant) contrast for a range of vergences.

Figure 6D:
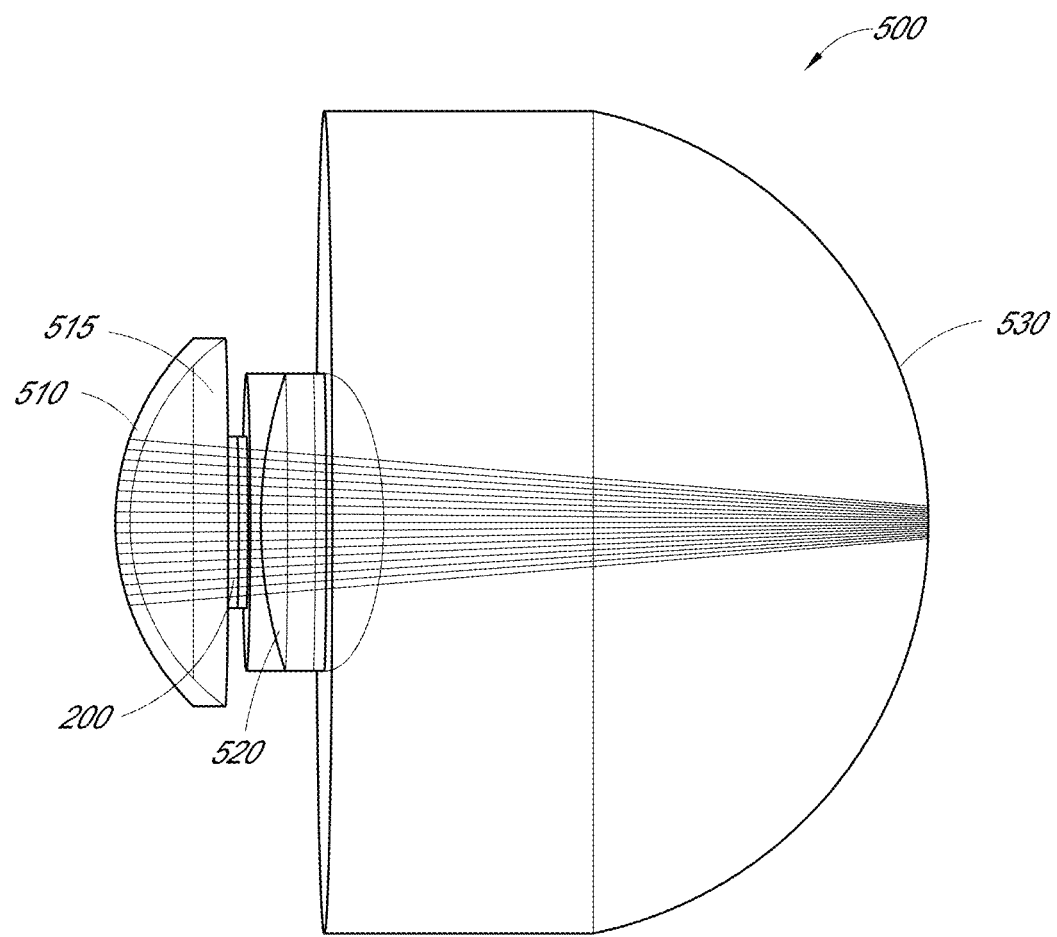
FIG. 6D schematically illustrates an example model to evaluate and design a lens in accordance with certain embodiments described herein.

In certain embodiments, the surface shape of the anterior surface 201a and/or the surface shape of the posterior surface 201b of the optic 201 can be evaluated and/or designed using the Liou-Brennan model eye such as under Best Corrected Distance Visual Acuity (BCDVA) conditions. FIG. 6D illustrates a schematic of an example phakic lens according to certain embodiments described herein modeled with the Liou-Brennan model eye. As shown in FIG. 6D, the lens 200 can be positioned between the iris 515 and in front of the "natural" crystalline lens 520 in the model. As also shown in FIG. 6D, the model can simulate light rays entering the eye 500 through the cornea 510, the lens 200, and the "natural" crystalline lens 520 and towards the retina 530. The model can be used for the polychromatic wavelengths between the range of about 400 nanometers to about 700 nanometers. The model can also be used with a dual-gradient index lens profile (e.g., to model astigmatism). Pseudophakic lenses according to certain embodiments described herein can also be modeled with the Liou-Brennan model eye with the lens positioned in place of the "natural" crystalline lens 520.

Other models known in the art or yet to be developed can also be used. For example, the surface shape of the anterior surface 201a and/or the surface shape of the posterior surface 201b of the optic 201 can also be evaluated and/or designed using a Badal model eye, an Arizona model eye (University of Arizona model), an Indiana model eye (Indiana University model), an ISO model eye, or any standardized or equivalent model eye. In addition, the simulations can be performed using ray tracing and/or design software known in the art or yet to be developed. As one example software, Zemax design software by Zemax, LLC in Redmond, Wash. can be used for some embodiments. The physical limitations of the environment, for example, the placement of the IOL anterior to the natural lens are useful for performing simulations for a phakic lens design. Such simulations can simultaneously evaluate performance (e.g., RMS wavefront error across the complete pupil) for multiple vergences an include contributions from the different vergences in a merit function that is optimized. Multiple wavefronts are thus evaluated in unison to arrive at a balanced design that provides substantially similar sized circles of confusion through a range of locations along the optical axis. Varying pupil size for different vergences can also be employed.

In certain embodiments, the surface shape of the anterior surface 201a and/or the surface shape of the posterior surface 201b of the optic 201 can be advantageously evaluated and designed such that for the visible wavelengths, light from an on-axis object is focused substantially on-axis, with substantially similar magnitude, and substantially on the retina within the range of at least about 0 Diopter to about 2.5 Diopter. By controlling the different orders of spherical aberrations (e.g., which can be correlated with the higher order aspheric terms in equation (2)) to achieve a substantially similar size cross-sections of the caustic for different longitudinal positions along the optical axis near the retina, and including the toric balancing and correction (e.g., the biconic term in equation (3)) when necessary to treat patients with astigmatism, the radial power profile of the lens 200 can be described as:

$$\Phi(r)=a+br^2+cr^4+dr^6+er^8, \quad (6)$$

where a, b, c, d, and e are real numbers. Additionally, in various embodiments, the surface shape of the anterior surface 201a and/or the surface shape of the posterior surface 201b of the optic 201 can be evaluated and designed to account for the Stiles-Crawford effect. Furthermore, the surface shapes can also be designed to consider the pupil sizes varying with illumination and/or object vergence.

In certain embodiments described herein, the design parameters (e.g., $R_y$, $k_y$, $R_x$, $k_x$, ratio $R_x/R_y$, and ratio $k_x/k_y$ for the posterior surface and/or R, k, $a_2$, $a_4$, $a_6$, and $a_8$ for the anterior surface) can be determined for the maximum aperture for the desired toric correction. For example, the toric correction with a relatively stable caustic for a maximum aperture of 4.0 mm may be different from the toric correction with a relatively stable caustic for a maximum aperture of 3.0 mm or 5.0 mm.

To describe the performance of the lens 200, the modulation transfer function (MTF) can be used in some embodiments. For example, the MTF can describe the ability of the lens 200 to transfer contrast at a particular resolution from the object to the image. In various embodiments of the lens 200, the anterior surface 201a and the posterior surface 201b can be shaped to provide MTF values for wavelengths between the range of about 400 nanometers to about 700 nanometers (weighted by photopic, scotopic and/or mesopic distributions) that are between about 0.1 and about 0.4 at spatial frequencies of about 100 line pairs per millimeter (e.g., 20/20 vision) for at least about 90%, at least about 95%, at least about 97%, at least about 98%, or at least about 99% of the object vergences within the range of at least about 0 Diopter to about 2.0, 2.1, 2.2, 2.3, 2.4 or 2.5 Diopter (or to about 2.6, 2.7, 2.8, 2.9, 3.0) when the optic 201 is inserted into an eye. For example, the eye could be a human eye having an aperture diameter of at least about 2 millimeters, at least about 3 millimeters, at least about 4 millimeters, for example, 2 to 6 millimeters, 3 to 6 millimeters, or 4 to 6 millimeters. The MTF values may thus be 0.1, 0.2, 0.3, or 0.4 or any range therebetween. Additionally, in various implementations, the anterior and posterior surfaces are shaped to provide modulation transfer functions without phase reversal for at least 90%, 95%, or 97%, up to 98%, 99%, or 100% of the object vergences within the range of 0 D to 2.5 D (or alternatively to 2.0, 2.1, 2.2, 2.3, 2.4, 2.6, 2.7, 2.8, 2.9, or 3.0 Diopter) when said optic is inserted into a model eye having an aperture size of 2 to 6 millimeters, 3 to 6 millimeters, or 4 to 6 millimeters. In some embodiments, when the human eye includes a crystalline lens, such MTF values can be provided when the optic 201 is inserted anterior of the crystalline lens. In other embodiments, when the human eye excludes a crystalline lens, such MTF values can be provided when the optic 201 is inserted in place of the crystalline lens. The MTF values may comprise average MTF values and may be calculated by integrating over the wavelength range which is weighted by any of the photopic, scotopic, mesopic distributions or combinations thereof.

As other examples, the eye could be a model eye (e.g., Liou-Brennan, Badal, Arizona, Indiana, ISO model eye, or any standardized or equivalent model eye) that models the human eye as opposed to a human eye itself. For example, the model eye in some embodiments can also include a Liou-Brennan model eye. In some embodiments, such MTF values can be provided when the optic 201 is inserted in the model eye in a phakic configuration. In other embodiments, such MTF values can be provided when the optic 201 is inserted in a pseudophakic configuration.

Other metrics to describe the performance of the lens 200 can also be used. For example, a normalized MTF metric, such as the Salvador Image Quality (SIQ) metric, can be used. The Salvador Image Quality metric can be described as:

$$SIQ = \left[\frac{AreaUnderMTFCurve(EyeOfInterest)}{AreaUnderMTFCurve(StdEye)}\right]_{0 \leq \xi \leq 100 \, mm^{-1}} \quad (7)$$

The Area Under MTF Curve can be the positive area under a given MTF curve, from zero to a spatial frequency $\zeta$ of 100 cycles/mm or the cutoff frequency, whichever appears first in the given plot. The "standard eye" can include a model eye (e.g., the Liou-Brennan model eye with a dilated, 6.0 mm diameter pupil) for the normalization. The MTF for the eye of interest can be the measured MTF of a given patient's eye, at a given wavelength (e.g., with a 6.0 mm dilated pupil). It can be measured and compared at the same angular field as the reference baseline. In the case of non-rotationally symmetric ocular systems, the results for Saggital SIQ and Tangential SIQ can be averaged. The Saggital SIQ can be calculated from the MTF in the XZ plane, whereas the Tangential SIQ can be calculated from the MTF in the YZ plane.

In various embodiments
SIQ≥1 "Fighter Pilot"
SIQ≈1 "Emmetropic Eye"
SIQ<1 Refractive Errors Present
SIQ<<1 Patient with Low Vision In certain embodiments described herein, the anterior and posterior surfaces can be shaped to provide a SIQ metric that is at least 0.6, 0.7, 0.8, 0.9, or 1 for at least 90%, 95%, or 97%, up to 98%, or 100% of the object vergences within the range of 0 to +1.5 D, 0 to +2.0 D, or 0 to +2.5 D when the optic is inserted into the human eye of the person whose correction is being provided having an aperture size of 4 to 6 millimeters (e.g., 4 mm, 5 mm, or 6 mm).

As another example, a psychophysical grade (e.g., standard psychophysical practices in imaging science) can be used to describe the performance of the lens. In certain embodiments described herein, the anterior and posterior surfaces can be shaped to provide an above average psychophysical grade (e.g., "good" or better) for at least 90%, 95%, or 97%, up to 98%, or 100% of the object vergences within the range of 0 to +1.5 D, 0 to +2.0 D, or 0 to +2.5 D when the optic is inserted into the human eye of the person whose correction is being provided having an aperture size of 4 to 6 millimeters (or into a model eye having an aperture size of 4 to 6 millimeters having vision similar to the person whose correction is being provided) Any grade lower than an above average psychophysical grade can determine the myopic edge for the performance of the lens. The myopic edge can be the limit of the near vision provided by the extended depth of field (e.g., +1.5 D, +2.0 D, or +2.5 D) of the lens.

Various implementations described herein comprise a single refractive lens that can be implanted in the eye, for example, posterior of the cornea. In certain implementations the refractive lens is configured to be implanted between the iris and the natural lens. In other implementations, the refractive lens is configured to be implanted in the capsular bag after removal of the natural lens. In various implementations, the refractive lens is not a diffractive lens and is devoid of a diffraction grating on the surfaces thereof. In various implementations, the refractive lens does not have discrete spaced apart foci. The anterior and posterior surfaces, for example, are shaped so as not to produce discrete foci where light is focused along the optical axis of the lens that are spaced apart from each other by regions where light is substantially less focused as provided in conventional multifocal lenses. Such multifocal design with discrete foci have multiple peaks of focused energy or of energy density at different locations on the optical axis.

Various implementations described herein can provide treatment for early onset and progression of presbyopia without need for laser surgery or reading glasses. Implementations may provide about 2.0D of near as well as intermediate viewing. Depth of field for range over 2 D for an aperture of 5.0 mm can be provided.

Various embodiments may be employed to provide modified monovision solutions. For example, a first lens may be provided that has an extended depth of focus for object vergences over 0 to 2.0 D or over 0 to 2.5 D and second lens may be provided that has an extended depth of focus for object vergences over −2.0 to 0 D or over −2.5 to 0 D. These respective lenses may be implanted in the patient's dominant and non-dominant respectively. A patient may then be provided with extended depth's of field that are different for each of the left and right eye. However the aggregate depth of field is larger than provided by one of the first or second lenses along. The design details of such lenses may otherwise be similar to those discussed above.

As described herein, various embodiments include a lens with extended depth of field. For example, with reference to lens 200 described herein (e.g., as shown in FIGS. 2-4), the lens 200 can include an optic 201 having an anterior surface 201a and/or a posterior surface 201b having a shape designed to increase the depth of field. In certain embodiments, the anterior surface and/or the posterior surface of the optic can also include a portion designed to improve distance vision (e.g. enhance distance visual acuity) yet still provide extended depth of field.

Figure 7A:
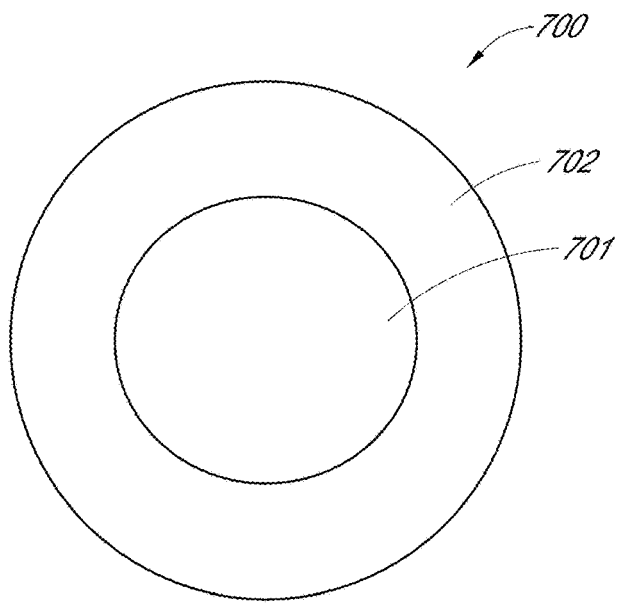
FIGS. 7A-7B are schematics for an example anterior surface and/or a posterior surface of an optic having a first portion configured to provide extended depth of field, and a second portion configured to provide enhanced distance visual acuity.
Figure 7B:
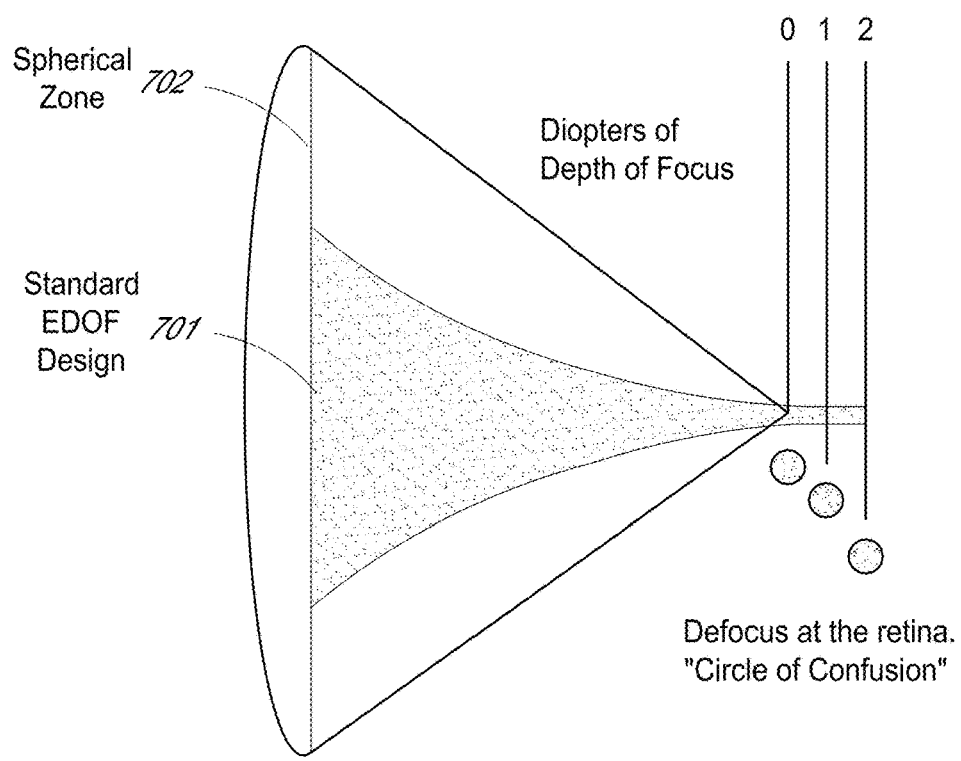

FIGS. 7A-7B are schematics for an example anterior surface and/or a posterior surface of such an optic. The anterior surface and the posterior surface can have a surface vertex. The optic can have an optical axis through the surface vertices. The anterior surface and/or a posterior surface of the example optic 700 can include a surface having a first portion 701 and a second portion 702. The first portion 701 can be configured to provide extended depth of field and the second portion 702 can be configured to provide monofocal distance correction and focusing. Referring to the defocus curves shown in FIG. 6C, the first portion 701 can have a defocus curve similar in shape to that of the "ideal" hyperfocal defocus curve, and the second portion 702 can have a defocus curve similar in shape to that of the standard spherical (monofocal) lens. Accordingly, the first portion 701 can be configured to provide extended depth of field, and the second portion 702 can be configured to provide enhanced distance vision or distance visual acuity. For example, the first portion 701 configured to provide an extended depth of field can supply near-equal visual acuity, or at least more than for the second portion 702, throughout a range of focus (e.g., far or distance, intermediate, near), while the second portion 702 can provide an enhanced vision quality metric for distance in comparison to the first portion 701. The enhanced vision quality metric can be a figure of merit for objects at distance (e.g., at or near 0.0 D). Objects between infinity and 2 meters (e.g., infinity to 2 meters, infinity to 3 meters, infinity to 4 meters, infinity to 5 meters, infinity to 6 meters, infinity to 7 meters, infinity to 8 meters, infinity to 9 meters, infinity to 10 meters, or any ranges in between any of these ranges) are considered distance. The figure of merit can be a modulation transfer function (MTF), a contrast sensitivity (CS), contrast, a derivation thereof, or a combination thereof. Other metrics can also be used to characterize image quality at the distance focus (which corresponds to the base power or labeled power of the lens) or for far objects. In some instances, the enhanced vision quality metric can be a higher value for the second portion 702 than for the first portion 701.

FIG. 7B illustrates how rays passing through the second portion 702 are focused on the distance vision focus (labeled as 0). (As referenced above, this distance vision focus corresponds to the base power, labeled power, or distance power of the lens.) In contrast, rays passing through the first portion 701 form a caustic of near constant diameter through the far (0), intermediate (1), and near (2) foci as opposed to a single sharp focus at the distance (0), intermediate (1) or near (2) planes thereby providing an extended depth of field.

As shown in FIGS. 7A-7B, the first portion 701 can be disposed centrally within the optic 700. In some cases, the first portion is disposed centrally about the optical axis. The first portion 701 can have a maximum cross-sectional diameter in the range of about 2.5-4.5 mm (e.g., 2.5 mm, 2.75 mm, 3.0 mm, 3.25 mm, 3.5 mm, 3.75 mm, 4.0 mm, 4.25 mm, 4.5 mm, or any ranges between any of these sizes). Larger or smaller sizes may also be possible. The first portion 701 can have a surface profile as described herein with respect to optic 201 to provide extended depth of field. For example, the first portion 701 may introduce spherical aberration to provide extended depth of field. In some such examples, as described herein, the first portion 701 can have a shape comprising a conic or a biconic envelope offset by perturbations from the envelope comprising an aspheric higher order function of radial distance from the optical axis. Equation (2) describes an example shape using a conic term and even-powered polynomial terms. Other examples and combinations are possible. For example, the first portion 701 can have a shape comprising a biaspheric envelope. The biaspheric envelope can include two aspheric cross-sections in two orthogonal directions. In some instances, the biaspheric envelope can be offset by perturbations comprising an aspheric higher order function of radial distance from the optical axis.

The second portion 702 can surround the first portion 701. The second portion 702 can extend from the first portion 701 to the end of the optic 700. Accordingly, in some examples, the width of the second portion 702 can be the distance between the outer periphery of the first portion 701 to the edge of the optic 700. For example, the second portion 702 can have a width (e.g., a distance between inner and outer radii) in the range of about 1.0-3.5 mm (e.g., 1.0 mm, 1.25 mm, 1.5 mm, 1.75 mm, 2.0 mm, 2.25 mm, 2.5 mm, 2.75 mm, 3.0 mm, 3.25 mm, 3.5 mm, or any ranges between any of these sizes). Sizes outside these ranges are also possible.

The second portion 702 can have a different surface profile than the first portion 701. The first portion 701 can have higher spherical aberration control that provides extended depth of field than the second portion 702. In some cases, the second portion 702 may have substantially no spherical aberration control or at least no aberration control that provides extended depth of focus. For example, the second portion 702 can have a shape that comprises a conic, biconic, or biaspheric envelope not offset by perturbations comprising an aspheric higher order function of radial distance from the optical axis. In some cases, the second portion can have a shape that is spherical.

The second portion 702 can allow greater control of the marginal rays of the system such that a higher percentage of the rays that propagate through this portion are focused on the retina potentially providing increased contrast or improved vision quality as measure by other metrics for objects at a distance such as at infinity in comparison to the first portion (e.g., for distance power or labeled power of about +6 to −18 D). This allows a more defined focus for distance (possibly a smaller spot at the distance plane for distance objects), yet still provides the extended depth of field provided by the first portion 701. Thus, the second portion 702 can increase the responsivity distance vision quality, creating an improvement in focusing objects at a distance. This improved distance vision can be perceived by a patient as an increase in brain-favored "positive" metrics, e.g., contrast sensitivity (CS).

In addition, as the first portion 701 is configured to provide an extended depth of field, it can supply near-equal visual acuity or vision, or at least more than the second portion 702, throughout a range of focus (or for a range of object distances). The spot size, wavefront of the lens, and quality (e.g., as measured by a figure of merit such as MTF or CS) at distance, intermediate, and near points are substantially similar. However, this attribute can create difficulties in evaluating the power of the lens using standard metrology. Post-operative clinical evaluation of a patient using classical Gaussian metrology methods can also be challenging. Any number of focal points could be labeled and found to be a valid base power (e.g., distance or label power). In certain embodiments, the second portion 702 directing a ring of marginal rays to a distance focus location can provide a repeatable measurement more closely corresponding to distance power. Likewise, the second portion 702 can provide a benefit in determination of the classical base power of the implanted or un-implanted lens, and can assist in the ability to accurately measure the power of the lens using industry standard metrology methods. Thus, certain embodiments described herein can allow for standardized measurement of a lens with extended depth of field, including, but not limited to, negative-powered, positive-powered, toric, or any combination therein.

In various embodiments described herein, the first portion 701 can allow for the usage of different orders of spherical aberration and of a conic, biconic, or biaspheric base curve in order to balance the entire wavefront at each of its points near the exit pupil of the implanted eye, and the second portion 702 can allow for enhanced distance vision and/or monofocal distance focusing and for use of standard metrology.

In various embodiments, the anterior surface and/or posterior surface of the optic 700 can include other portions. For example, the anterior surface and/or the posterior surface of the optic 700 can further include a transition portion (not shown) providing a smooth transition without discontinuity between the first portion 701 and the second portion 702. The transition portion can also allow for additional wavefront optimization. In some embodiments, the transition portion can have a width (e.g., distance between the inner radii and the outer radii) in the range of about 0 to 1 mm (e.g., 0 mm, 0.1 mm, 0.2 mm, 0.3 mm, 0.4 mm, 0.5 mm, 0.6 mm, 0.7 mm, 0.8 mm, 0.9 mm, 1.0 mm, or any ranges between any of these sizes). Values outside these ranges are also possible. In some instances, the transition between the curvatures of the first portion 701 and the second portion 702 can be smooth enough that no transition region is desired.

Figure 8A:
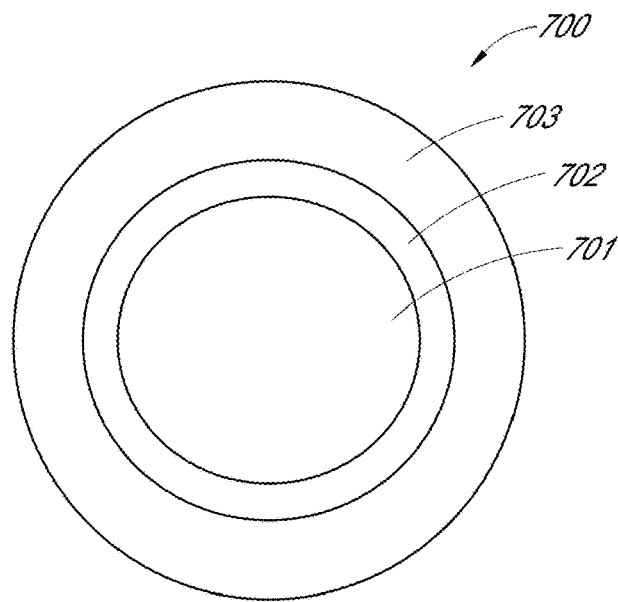
FIGS. 8A-8B are schematics for another example anterior surface and/or a posterior surface of an optic having a first portion configured to provide extended depth of field, and a second portion configured to provide enhanced distance visual acuity.
Figure 8B:
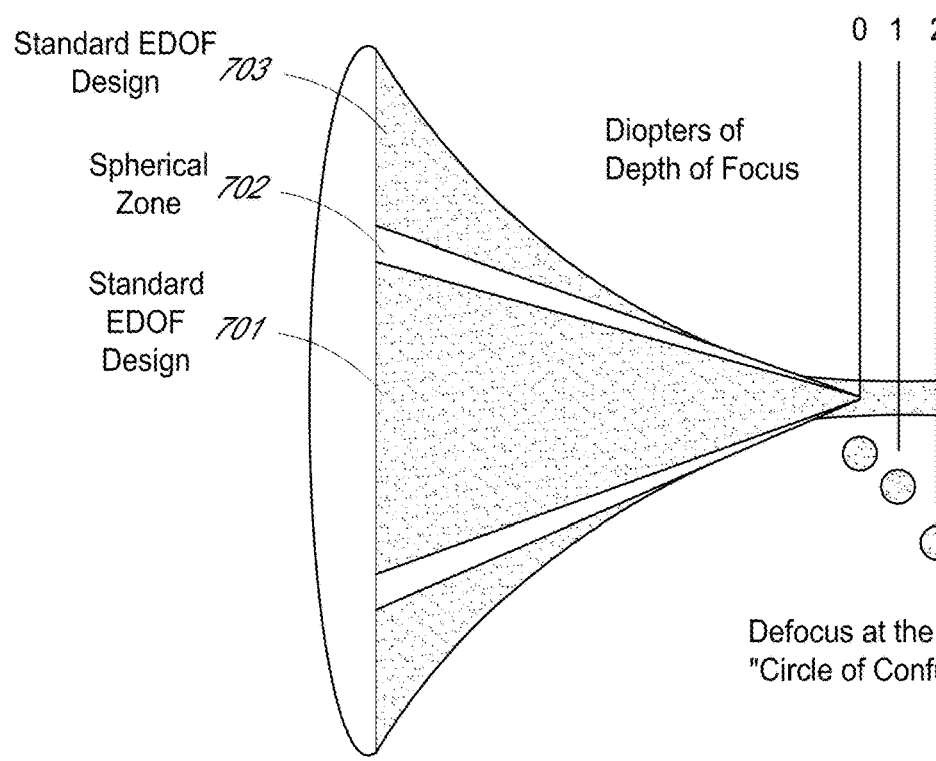

FIGS. 8A-8B are schematics for another example anterior surface and/or a posterior surface of an optic having a first portion configured to provide extended depth of field, and a second portion configured to provide enhanced distance visual acuity. In this example, the anterior surface and/or the posterior surface of the optic 700 can include a first portion 701 and a second portion 702 as in FIGS. 7A-7B. As shown in FIGS. 8A-8B, the anterior surface and/or the posterior surface of the optic 700 also can include a third portion 703 surrounding the second portion 702. In some such embodiments, the first portion 701 can have a maximum cross-sectional diameter in the range of about 2.5-4.5 mm (e.g., 2.5 mm, 2.75 mm, 3.0 mm, 3.25 mm, 3.5 mm, 3.75 mm, 4.0 mm, 4.25 mm, 4.5 mm, or any ranges between any of these sizes). The second portion 702 can be described as an annulus having a width between the inner and outer radii in the range of about 0.25-1.5 mm (e.g., 0.25 mm, 0.5 mm, 0.75 mm, 1.0 mm, 1.25 mm, 1.5 mm, or any ranges between any of these sizes). Furthermore, the third portion 703 can extend from the second portion 702 to the end of the optic 700. Accordingly, in some examples, the width of the third portion 703 can be the distance between the outer periphery of the second portion 702 to the edge of the optic 700. For example, the third portion 703 can have a width (e.g., distance between inner and outer radii) in the range of about 0.5-3.5 mm (e.g., 0.5 mm, 0.75 mm, 1.0 mm, 1.25 mm, 1.5 mm, 1.75 mm, 2.0 mm, 2.25 mm, 2.5 mm, 2.75 mm, 3.0 mm, 3.5 mm, or any ranges between any of these sizes). Values outside these ranges are also possible.

FIG. 8B illustrates how rays passing through the second portion 702 are focused on the distance vision focus (labeled as 0). In contrast, rays passing through the first portion 701 and third portion 703 focus continuously through the far (0), intermediate (1), and near (2) foci thereby providing an extended depth of field. As discussed above, the rays passing through the first portion 701 and third portion 703 form a caustic having nearly constant cross-section or beam diameter at the far (0), intermediate (1), and near (2) planes. This beam diameter, however, may potentially be larger than the size of the focus spot at the far image plane (0) formed by the rays propagating solely through of the second portion 702.

The third portion 703 can have a different surface profile than the second profile 702. For example, the third portion 703 can have higher spherical aberration control that provides extended depth of field than the second portion 702. In some examples, the third portion 703 can have a shape that comprises a conic, biconic, or biaspheric envelope offset by perturbations comprising an aspheric higher order function of radial distance from the optical axis.

In some embodiments, the third portion 703 can have a similar surface profile and/or substantially the same spherical aberration control as the first portion 701. For example, the third portion 703 can have substantially the same conic, biconic, or biaspheric envelope offset by perturbations with respect to the envelope comprising an aspheric higher order function of radial distance from the optical axis as the first portion.

As described herein, the first portion 701 and/or the third portion 703 can have a shape that comprises a conic, biconic, biaspheric envelope offset by perturbations comprising an aspheric higher order function of radial distance from the optical axis. In various embodiments, the aspheric higher order function can include at least one even order term, $a_{2n}r^{2n}$, where n is an integer and $a_{2n}$ is a coefficient and r is the radial distance from the optical axis. For example, the aspheric higher order function can include a second order term, $a_2 r^2$, where $a_2$ is a coefficient and r is the radial distance from the optical axis. The aspheric higher order function can include a fourth order term, $a_4 r^4$, where $a_4$ is a coefficient and r is the radial distance from the optical axis. The aspheric higher order function can also include a sixth order term, $a_6 r^6$ where $a_6$ is a coefficient and r is the radial distance from the optical axis. The aspheric higher order function can further include an eighth order term, $a_8 r^8$ where $a_8$ is a coefficient and r is the radial distance from the optical axis. The aspheric higher order function can include any combination of these higher order terms and possibly more terms.

In various embodiments, the anterior surface and/or the posterior surface of the optic 700 can further include a transition portion (not shown) providing a smooth transition without discontinuity between the second portion 702 and the third portion 703. The transition portion can also allow for additional wavefront optimization. In some embodiments, the transition portion can have a width (e.g., distance between the inner radii and the outer radii) in the range of about 0 to 1 mm (e.g., 0 mm, 0.1 mm, 0.2 mm, 0.3 mm, 0.4 mm, 0.5 mm, 0.6 mm, 0.7 mm, 0.8 mm, 0.9 mm, 1.0 mm, or any ranges between any of these sizes). Dimensions outside these ranges are also possible. In some instances, the transition between the curvatures of the second portion 702 and the third portion 703 can be smooth enough that no transition region is desired.

In some embodiments, the caustic of the second portion 702 can be sculpted to blend smoothly (or to provide a smoother transition) with the caustic of the first portion 701 and/or the caustic of the third portion 703. For example, as shown in FIG. 8B, the lower caustic envelope of the second portion 702 may not blend smoothly with the lower caustic envelope of the third portion 703 (e.g., see the discontinuity near the intersection of the caustics). Accordingly, in some embodiments, to provide a smoother caustic transition, the conic constant of the conic, biconic, or biaspheric envelope of the second portion 702 may be such to blend smoother with the caustic of the first portion 701 and/or the caustic of the third portion 703 (e.g., to fit more tightly with the ray envelope of the first portion 701 and/or to fit more tightly with the ray envelope of the third portion 703). For example, in some embodiments, the second portion 702 can have a conic constant such that the caustic of the second portion 702 blends smoothly with the caustic of the first portion 701, for example, more smoothly than if the second portion comprises a spherical surface. Furthermore, in some embodiments, the second portion 702 can have a conic constant such that the caustic of the second portion 702 blends smoothly with the caustic of the third portion 703, for example, more smoothly than if the second portion comprises a spherical surface. By having a smoother caustic transition, a slight misalignment in the surgical placement of the implants may be expected to produce a less noticeable effect on a patient's vision. In addition, with a smoother caustic transition, superimposed ghosting may potentially be reduced.

The various disclosures with respect to the optic 201 described herein can also apply to the various embodiments of FIGS. 7A-8B. For example, certain embodiments of FIGS. 7A-8B can be used for phakic or pseudophakic lens implants as described herein. In embodiments used for phakic lens implants, the optic 700 can have a thickness along the optical axis that is about 100-700 micrometers, about 100 to about 600 micrometers, about 100 to about 500 micrometers, about 100 to about 400 micrometers, about 100 to about 300 micrometers, or about 100 to about 200 micrometers (e.g., 100 micrometers, 200 micrometers, 300 micrometers, 400 micrometers, 500 micrometers, 600 micrometers, 700 micrometers, any value in between such ranges, or any range formed by such values). In embodiments for pseudophakic lens implants, the thickness along the optical axis can be about 700 micrometers to about 4 mm, about 700 micrometers to about 3 mm, about 700 micrometers to about 2 mm, about 700 micrometers to about 1 mm, any value in between such ranges, or any range formed by any values in these ranges. As another example, various embodiments of FIGS. 7A-8B can be used in a lens comprising at least one haptic disposed with respect to the optic 700 to affix the optic 700 in the eye when implanted therein. Furthermore, in some instances, the first portion 701 can be on the anterior surface of the optic, and the second portion 702 can be on the posterior surface of the optic. Likewise, in some instances, the first portion 701 can be on the posterior surface of the optic, and the second portion 702 can be on the anterior surface of the optic.

The terms "about" and "substantially" as used herein represent an amount equal to or close to the stated amount (e.g., an amount that still performs a desired function or achieves a desired result). For example, unless otherwise stated, the terms "about" and "substantially" may refer to an amount that is within (e.g., above or below) 10% of, within (e.g., above or below) 5% of, within (e.g., above or below) 1% of, within (e.g., above or below) 0.1% of, or within (e.g., above or below) 0.01% of the stated amount.

Various embodiments of the present invention have been described herein. Although this invention has been described with reference to these specific embodiments, the descriptions are intended to be illustrative of the invention and are not intended to be limiting. Various modifications and applications may occur to those skilled in the art without departing from the true spirit and scope of the invention.

What is claimed is:

1. A lens configured for implantation into an eye of a human, said lens comprising:
   an optic comprising transparent material, said optic having an anterior surface and a posterior surface, each of said anterior surface and said posterior surface having a surface vertex, said optic having an optical axis through said surface vertices,
   at least one haptic disposed with respect to the optic to affix the optic in the eye when implanted therein,
   wherein said anterior and posterior surfaces comprise aspheric surfaces and said posterior surface has an aspheric shape that comprises a biconic offset by perturbations comprising an aspheric higher order function of radial distance from the optical axis,
   wherein the posterior surface has a radius of curvature, $R_y$, a radius of curvature, $R_x$, a conic constant, $k_y$, and a conic constant, $k_x$,
   wherein the posterior surface has an absolute value of ratio $R_x/R_y$ between 0 and 100 and an absolute value of ratio $k_x/k_y$ between 0 and 100, and
   wherein the anterior surface has a radius of curvature between 0 to 1 mm.

2. The lens of claim 1, wherein the absolute value of the ratio $R_x/R_y$ is between 0 and 75.

3. The lens of claim 2, wherein the absolute value of the ratio $R_x/R_y$ is between 0 and 50.

4. The lens of claim 3, wherein the absolute value of the ratio $R_x/R_y$ is between 0 and 25.

5. The lens of claim 4, wherein the absolute value of the ratio $R_x/R_y$ is between 0 and 10.

6. The lens of claim 5, wherein the absolute value of the ratio $R_x/R_y$ is between 0.1 and 10.

7. The lens of claim 6, wherein the absolute value of the ratio $R_x/R_y$ is between 0.2 and 10.

8. The lens of claim 7, wherein the absolute value of the ratio $R_x/R_y$ is between 0.25 and 10.

9. The lens of claim 8, wherein the absolute value of the ratio $R_x/R_y$ is between 0.5 and 10.

10. The lens of claim 1, wherein the absolute value of the ratio $k_x/k_y$ is between 0 and 75.

11. The lens of claim 10, wherein the absolute value of the ratio $k_x k_y$ is between 0 and 50.

12. The lens of claim 11, wherein the absolute value of the ratio $k_x/k_y$ is between 0 and 25.

13. The lens of claim 12, wherein the absolute value of the ratio $k_x/k_y$ is between 0 and 10.

14. The lens of claim 13, wherein the absolute value of the ratio $k_x/k_y$ is between 0.1 and 10.

15. The lens of claim 14, wherein the absolute value of the ratio $k_x/k_y$ is between 0.2 and 10.

16. The lens of claim 15, wherein the absolute value of the ratio $k_x/k_y$ is between 0.25 and 10.

17. The lens of claim 16, wherein the absolute value of the ratio $k_x/k_y$ is between 0.5 and 10.

18. The lens of claim 1, wherein said optic comprises an exit pupil, and
   wherein the anterior and posterior surfaces are shaped to provide a radial power profile characterized by $\Phi(r)= a+br^2+cr^4+dr^6+er^8$ for wavefront at the exit pupil of the optic for an object vergence of 0 to 2.5 Diopter (D) where r is the radial distance from the optical axis and a, b, c, d, and e are coefficients.

19. The lens of claim 1, wherein a thickness along said optical axis is between about 100-700 micrometers.

20. The lens of claim 1, wherein said anterior surface is convex and said posterior surface is concave such that said optic is meniscus shaped.

21. The lens of claim 1, wherein the anterior surface has a radius of curvature between $1\times10^{-6}$ to $1\times10^{-3}$ mm.

22. The lens of claim 21, wherein the anterior surface has a radius of curvature between $5\times10^{-6}$ to $5\times10^{-4}$ mm.

23. The lens of claim 1, wherein the anterior surface has a conic constant between $-1\times10^6$ to $-100$.

24. The lens of claim 23, wherein the anterior surface has a conic constant between $-3\times10^5$ to $-2\times10^5$.

25. The lens of claim 1, wherein the posterior surface radius of curvature, $R_y$, is between 0 to 20 mm.

26. The lens of claim 1, wherein the posterior surface a radius of curvature, $R_x$, is between 0 to 20 mm.

27. The lens of claim 1, wherein the posterior surface conic constant, $k_y$, is between $-20$ to 20.

28. The lens of claim 1, wherein the posterior surface conic constant, $k_x$, is between $-25$ to 0.

* * * * *